US010920245B2

(12) United States Patent
O'Riordan et al.

(10) Patent No.: US 10,920,245 B2
(45) Date of Patent: Feb. 16, 2021

(54) GENE THERAPY FOR AMYOTROPHIC LATERAL SCLEROSIS AND OTHER SPINAL CORD DISORDERS

(71) Applicant: Genzyme Corporation, Cambridge, MA (US)

(72) Inventors: Catherine O'Riordan, Bridgewater, NJ (US); Samuel Wadsworth, Shrewsbury, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/858,303

(22) Filed: Dec. 29, 2017

(65) Prior Publication Data

US 2018/0230490 A1 Aug. 16, 2018

Related U.S. Application Data

(60) Division of application No. 12/417,910, filed on Apr. 3, 2009, now Pat. No. 9,890,394, which is a continuation of application No. PCT/US2007/021272, filed on Oct. 3, 2007.

(60) Provisional application No. 60/827,977, filed on Oct. 3, 2006.

(51) Int. Cl.
| | |
|---|---|
| *C12N 15/86* | (2006.01) |
| *C07H 21/04* | (2006.01) |
| *A61K 39/00* | (2006.01) |
| *A61K 38/17* | (2006.01) |
| *A61K 48/00* | (2006.01) |

(52) U.S. Cl.
CPC .......... *C12N 15/86* (2013.01); *A61K 38/1709* (2013.01); *A61K 48/0075* (2013.01); *A61K 48/005* (2013.01); *C07K 2319/00* (2013.01); *C12N 2750/14143* (2013.01); *C12N 2750/14145* (2013.01); *C12N 2810/6027* (2013.01); *C12N 2830/002* (2013.01); *C12N 2830/15* (2013.01)

(58) Field of Classification Search
CPC ..... C12N 15/86; C07H 21/04; C07K 2319/00
USPC ........... 435/320.1; 424/192.1; 536/23.4, 23.5
See application file for complete search history.

(56) References Cited

U.S. PATENT DOCUMENTS

| | | | |
|---|---|---|---|
| 6,042,576 | A | 3/2000 | DeVries |
| 6,432,927 | B1 | 8/2002 | Gregory et al. |
| 6,838,430 | B2 | 1/2005 | Arbeit |
| 7,053,062 | B2 | 5/2006 | Gregory et al. |
| 9,890,394 | B2 | 2/2018 | O'Riordan et al. |
| 2003/0104973 | A1 | 5/2003 | Einat et al. |
| 2005/0202450 | A1 | 9/2005 | Huang |

FOREIGN PATENT DOCUMENTS

| | | | |
|---|---|---|---|
| EP | 0 130 166 | A1 | 1/1985 |
| EP | 2 066 791 | B1 | 6/2009 |
| WO | WO-03/055983 | A2 | 7/2003 |

OTHER PUBLICATIONS

Pajusola et al., 2005, The FASEB Journal, vol. 19, express article, pp. 1-16.*
Wadsworth et al., 2004, US 20040002468 A1.*
Scheule et al., 2008, US 20080025952, effective filing date, Dec. 1, 2004.*
Bennett, G. et al. (Aug. 2000). Future Directions in the Management of Pain by Intraspinal Drug Delivery, *Journal of Pain and Symptom Management* 20(2):S44-S50.
Boilee, S. et al. (May 2004). "Gene Therapy for ALS Delivers," *Trends in Neurosciences* 27(5):235-238.
Brockington, A. et al. (2004). "Vascular Endothelial Growth Factor and the Nervous System," *Neuropathology and Applied Neurobiology* 30:427-446.
Bryan et al., 2013, http://www.elsevierblogs.com/currentcomments/?p=962, Implications of protein fold switching, p. 1-4.
Chattopadhyay et al. (Feb. 2004). "Effect of Single Amino Acid Mutations in the Conserved GDNQ Motif of L Protein of Rinderpest Virus on RNA Synthesis in Vitro and in Vivo," *Virus Research* 99:139-145.
Choi, V. W. et al. (Jun. 2005). "AAV Hybrid Serotypes: Improved Vectors for Gene Delivery," *Curr. Gene Ther.* 5(3):299-310, 20 pages.
Extended European Search Report dated Aug. 9, 2012, for European Patent Application No. 12157957.7, filed on Oct. 3, 2007, 4 pages.
Extended European Search Report dated Jan. 27, 2017, for European Patent Application No. 16184966.6, filed on Aug. 19, 2016, 7 pages.
Extended European Search Report dated Oct. 5, 2010, for European Patent Application No. 07839216.4, filed on Oct. 3, 2007, 6 pages.
Flotte, T. (Jun. 2005). "Recent developments in recombinant AAV-mediated gene therapy for lung Diseases" *Current Gene Therapy* 5(3):361-366.

(Continued)

*Primary Examiner* — Shin Lin Chen
(74) *Attorney, Agent, or Firm* — Morrison & Foerster LLP

(57) ABSTRACT

This disclosure provides methods and compositions for treating disorders or injuries that affect motor function and control in a subject. In one aspect, the invention a transgene product is delivered to a subject's spinal cord by administering a recombinant viral vector containing the transgene to the spinal cord. The viral vector delivers the transgene which expresses the encoded recombinant viral gene product. The viral gene product comprises HIF1-alpha. Also provided are compositions for delivery of a transgene product to a subject's spinal cord.

3 Claims, 6 Drawing Sheets

Specification includes a Sequence Listing.

(56) References Cited

OTHER PUBLICATIONS

Gao et al. (Sep. 3, 2002). "Novel Adeno-Associated Viruses from Rhesus Monkeys as Vectors for Human Gene Therapy," *PNAS* 99(18):11854-11859.

Gendron, N.H. et al. (Apr. 1999). "Spinal Muscular Atrophy: Molecular Pathophysiology," *Curr. Opin. Neurol.* 12(2):137-142.

Gorecki, D. (Oct. 2001). "Prospects and Problems of Gene Therapy: An Update," *Expert Opin. Emerging Drugs* 6(2):187-198.

Iwasaki, Y. et al. (Oct. 2002). "Protective Effect of Interleukin-3 and Erythropoietin on Motor Neuron Death After Neonatal Axotomy," *Neurol. Res.* 24:643-646.

Kaspar, B.K. et al. (Aug. 8, 2003). "Retrograde Viral Delivery of IGF-1 Prolongs Survival in a Mouse ALS Model," *Science* 301:839-842.

Kodama, K. (2006). "The Features and Shortcomings for Gene Delivery of Current Non-Viral Carriers," *Current Medicinal Chemistry* 13(18):2155-2161.

Lebedeva, I.V. et al. (Apr. 2003). "Restoring Apoptosis as a Strategy for Cancer Gene Therapy: Focus on p53 and mda-7," *Seminars in Cancer Biology* 13(2):169-178.

Lefebvre, S. et al. (Jul. 1997). "Correlation Between Severity and SMN protein Level in Spinal Muscular Atrophy," *Nature Genetics* 16:265-269.

Madsen, A. (Sep. 1, 2010). "Building a Better Mouse: How Animal Models Help Fight ALS," Muscular Dystrophy Association—USA, located at <http://alsn.mda.org/article/building-better-mouse-how-animal-models-help-fight-als>, last visited on Jul. 24, 2014, 4 pages.

Pajusola, K. et al. (Aug. 2005, e-pub. Jun. 15, 2005). "Stabilized HIF-1α is superior to VEGF for angiogenesis in skeletal muscle via adeno-associated virus gene transfer," *FASEB J.* 19(10):1365-1367.

Pandey, Prativa, 2007, Abstracts, 59th Southeast regional Meeting of the American Chemical Society, Greenville, SC, United States, GEN-671, Publisher: American Chemical Society, Washington D.C.

Piskacek, S. et al. (Jun. 2007, e-pub. Apr. 30, 2007). "Nine-amino-acid transactivation domain: Establishment and prediction utilities," *Genomics* 89(6): 756-768.

Ruitenberg, M.J. et al. (2002). "Adeno-associated Viral Vectors as Agents for Gene Delivery: Application in Disorders and Trauma of the Central Nervous System," *Methods* 28:182-194.

Sau, D. et al. (2007). "Mutation of SOD1 in ALS: A Gain of a Loss of Function," *Human Molecular Genetics* 16(13):1604-1618.

Shaw, P.J. (Sep. 2001). Mechanisms of Cell Death and Treatment Prospects in Motor Neuron Disease, *HKMJ* 7(3):267-280.

Skolnick, J. et al. (Jan. 2000). "From genes to protein structure and function: novel applications of computational approaches in the genomic era," *Trends in Biotech* 18(1):34-39.

Sköld, M.K. et al. (2004). "Induction of HIF1α but not HIF2α in Motoneurons After Ventral funiculus Axotomy-Implication in Neuronal Survival Strategies," *Experimental Neurology* 188:20-32.

Smallwood, S. et al. (Dec. 2002). "Different Substitutions at Conserved Amino Acids in Domains II and III in the Sendai L RNA Polymerase Protein Inactivate Viral RNA Synthesis," *Virology* 304(1):135-145.

Storkebaum, E. et al. (2004). "VEGF:Once Regarded as a Specific Angiogenic Factor, Now Implicated in Neuroprotection," *Bioessays* 26:943-954.

Thomas C.E. et al. (May 2003). "Progress and Problems with the Use of Viral Vectors for Gene Therapy," *Nature Reviews Genetics* 4(5):346-358.

Tomasinsig, L. et al. (Feb. 2005). "The Cathelicidins—Structure, Function and Evolution," *Current Protein and Peptide Science* 6(1):23-34.

Zaiss, A.K. et al. (Jun. 2005). "Immune Responses to Adeno-Associated Virus Vectors," *Current Gene Therapy* 5(3):323-331.

\* cited by examiner

Fig. 1. Spinal Cord Vector Genomes

Fig. 2. Brain Vector Genomes

Fig. 3. Muscle Vector Genomes

SEQUENCE LISTING

<160> NUMBER OF SEQ ID NOS: 7

<210> SEQ ID NO 1
<211> LENGTH: 1430
<212> TYPE: DNA
<213> ORGANISM: Homo sapiens

<400> SEQUENCE: 1

| | | | | | |
|---|---|---|---|---|---|
| atggagggcg | ccggcggcgc | gaacgacaag | aaaaagataa | gttctgaacg | tcgaaaagaa | 60 |
| aagtctcgag | atgcagccag | atctcggcga | agtaaagaat | ctgaagtttt | ttatgagctt | 120 |
| gctcatcagt | tgccacttcc | acataatgtg | agttcgcatc | ttgataaggc | ctctgtgatg | 180 |
| aggcttacca | tcagctattt | gcgtgtgagg | aaacttctgg | atgctggtga | tttggatatt | 240 |
| gaagatgaca | tgaaagcaca | gatgaattgc | ttttatttga | aagccttgga | tggttttgtt | 300 |
| atggttctca | cagatgatgg | tgacatgatt | tacatttctg | ataatgtgaa | caaatacatg | 360 |
| ggattaactc | agtttgaact | aactggacac | agtgtgtttg | attttactca | tccatgtgac | 420 |
| catgaggaaa | tgagagaaat | gcttacacac | agaaatggcc | ttgtgaaaaa | gggtaaagaa | 480 |
| caaaacacac | agcgaagctt | ttttctcaga | atgaagtgta | ccctaactag | ccgaggaaga | 540 |
| actatgaaca | taaagtctgc | aacatggaag | gtattgcact | gcacaggcca | cattcacgta | 600 |
| tatgatacca | acagtaacca | acctcagtgt | gggtataaga | aaccacctat | gacctgcttg | 660 |
| gtgctgattt | gtgaacccat | tcctcaccca | tcaaatattg | aaattccttt | agatagcaag | 720 |
| actttcctca | gtcgacacag | cctggatatg | aaatttttctt | attgtgatga | agaattacc | 780 |
| gaattgatgg | gatatgagcc | agaagaactt | ttaggccgct | caatttatga | atattatcat | 840 |
| gctttggact | ctgatcatct | gaccaaaact | catcatgata | tgtttactaa | aggacaagtc | 900 |
| accacaggac | agtacaggat | gcttgccaaa | agaggtggat | atgtctgggt | tgaaactcaa | 960 |
| gcaactgtca | catataacac | caagaattct | caaccacagt | gcattgtatg | tgtgaattac | 1020 |
| gttgtgagtg | gtattattca | gcacgacttg | atttttctccc | ttcaacaaac | agaatgtgtc | 1080 |
| cttaaaccgg | ttgaatcttc | agatatgaaa | atgactcagc | tattcaccaa | agttgaatca | 1140 |
| gaagatacaa | gtagcctctt | tgacaaactt | aagccggatt | cccggggatc | tgggcccccc | 1200 |
| cgaccgatgt | cagcctgggg | gacgagctcc | acttagacgg | cgaggacgtg | gcgatggcgc | 1260 |
| atgccgacgc | gctagacgat | ttcgatctgg | acatgttggg | ggacggggat | tccccggggc | 1320 |
| cgggatttac | ccccccacgac | tccgcccccct | acggcgctct | ggatatggcc | gacttcgagt | 1380 |
| ttgagcagat | gtttaccgat | gcccttggaa | ttgacgagta | cggtgggtag | | 1430 |

<210> SEQ ID NO 2
<211> LENGTH: 1174
<212> TYPE: DNA
<213> ORGANISM: Homo sapiens

<400> SEQUENCE: 2

| | | | | | |
|---|---|---|---|---|---|
| atggagggcg | ccggcggcgc | gaacgacaag | aaaaagataa | gttctgaacg | tcgaaaagaa | 60 |
| aagtctcgag | atgcagccag | atctcggcga | agtaaagaat | ctgaagtttt | ttatgagctt | 120 |
| gctcatcagt | tgccacttcc | acataatgtg | agttcgcatc | ttgataaggc | ctctgtgatg | 180 |
| aggcttacca | tcagctattt | gcgtgtgagg | aaacttctgg | atgctggtga | tttggatatt | 240 |
| gaagatgaca | tgaaagcaca | gatgaattgc | ttttatttga | aagccttgga | tggttttgtt | 300 |
| atggttctca | cagatgatgg | tgacatgatt | tacatttctg | ataatgtgaa | caaatacatg | 360 |
| ggattaactc | agtttgaact | aactggacac | agtgtgtttg | attttactca | tccatgtgac | 420 |

```
catgaggaaa tgagagaaat gcttacacac agaaatggcc ttgtgaaaaa gggtaaagaa    480
caaaacacac agcgaagctt ttttctcaga atgaagtgta ccctaactag ccgaggaaga    540
actatgaaca taaagtctgc aacatggaag gtattgcact gcacaggcca cattcacgta    600
tatgatacca acagtaacca acctcagtgt gggtataaga aaccacctat gacctgcttg    660
gtgctgattt gtgaacccat tcctcaccca tcaaatattg aaattccttt agatagcaag    720
actttcctca gtcgacacag cctggatatg aaattttctt attgtgatga agaattacc     780 gaattgatgg gatatgagcc agaagaactt ttaggccgct caatttatga atattatcat    840
gctttggact ctgatcatct gaccaaaact catcatgata tgtttactaa aggacaagtc    900
accacaggac agtacaggat gcttgccaaa agaggtggat atgtctgggt tgaaactcaa    960
gcaactgtca catataacac caagaattct caaccacagt gcattgtatg tgtgaattac    1020
gttgtgagtg gtattattca gcacgacttg attttctccc ttcaacaaaa cagaatgtgt    1080
ccttaaaccg gttgaatctt cagatatgaa aatgactcag ctattcacca aagttgaatc    1140
agaagataca agtagcctct ttgacaaaact taag                               1174

<210> SEQ ID NO 3
<211> LENGTH: 475
<212> TYPE: DNA
<213> ORGANISM: Homo sapiens

<400> SEQUENCE: 3
ccggaattcc cggggatctg ggccccccg accgatgtca gcctggggga cgagctccac       60
ttagacggcg aggacgtggc gatggcgcat gccgacgcgc tagacgattt cgatctggac    120
atgttggggg acggggattc cccggggccg ggatttaccc ccacgactc cgcccctac      180 ggcgctctgg atatggccga cttcgagttt gagcagaccg gaattcccgg ggatctgggc    240 cccccgacc gatgtcagcc tggggacga gctccactta gacggcgagg acgtggcgat      300
ggcgcatgcc gacgcgctag acgatttcga tctggacatg ttgggggacg gggattcccc    360
ggggccggga tttaccccc acgactccgc ccctacggc gctctggata tggccgactt      420
cgagtttgag cagatgttta ccgatgccct tggaattgac gagtacggtg ggtag          475

<210> SEQ ID NO 4
<211> LENGTH: 38
<212> TYPE: DNA
<213> ORGANISM: Artificial Sequence
<220> FEATURE:
<223> OTHER INFORMATION: PCR primer

<400> SEQUENCE: 4
ggggtacctt ctcttctccg cgtgtggagg gagccagc                              38

<210> SEQ ID NO 5
<211> LENGTH: 37
<212> TYPE: DNA
<213> ORGANISM: Artificial Sequence
<220> FEATURE:
<223> OTHER INFORMATION: PCR primer

<400> SEQUENCE: 5
gctctagagt gagccaccag tgtccaaaaa aaggatg                               37

<210> SEQ ID NO 6
<211> LENGTH: 33
<212> TYPE: DNA
```

```
<213> ORGANISM: Artificial Sequence
<220> FEATURE:
<223> OTHER INFORMATION: PCR primer

<400> SEQUENCE: 6
cgtacgctta agccggaatt cccggggatc tgg                           33

<210> SEQ ID NO 7
<211> LENGTH: 32
<212> TYPE: DNA
<213> ORGANISM: Artificial Sequence
<220> FEATURE:
<223> OTHER INFORMATION: PCR primer

<400> SEQUENCE: 7
cgctctagac tacccaccgt actcgtcaat tc                            32
```

GENE THERAPY FOR AMYOTROPHIC LATERAL SCLEROSIS AND OTHER SPINAL CORD DISORDERS

CROSS REFERENCE TO RELATED APPLICATIONS

This application is a divisional of U.S. patent application Ser. No. 12/417,910, filed Apr. 3, 2009 (now U.S. Pat. No. 9,890,394), which is a continuation of International Application No. PCT/US07/21272, filed Oct. 3, 2007, which claims priority benefit of U.S. Provisional Application No. 60/827,977, filed Oct. 3, 2006, the contents of each are hereby incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792009710SEQLIST.txt, date recorded: Dec. 28, 2017, size: 5 KB).

FIELD OF THE INVENTION

The present invention relates to compositions and methods for treating disorders affecting a subject's motor function and in particular, motor function affected by disease or injury to the brain and/or spinal cord.

BACKGROUND OF THE INVENTION

Amyotrophic lateral sclerosis (ALS) is a progressive, neurodegenerative condition involving the loss of large motor neurons in the brain and spinal cord. It is characterized by progressive weakness, atrophy and spasticity, leading to paralysis and respiratory failure within five years of onset. Familial ALS accounts for 10% of all ALS cases; approximately 25% of these cases are due to mutations in the Cu/Zn superoxide dismutase gene (SOD1) [1]. To date 109 different mutations have been identified in the SOD1 gene; these span all five exons [2]. Besides very rare mutations in genes for heavy neurofilament chain (NFH), dynactin, vesicular binding protein 1 gene and the ALSIN gene, SOD1 is the only major ALS susceptibility locus identified. SOD1 is a mainly cytoplasmic enzyme that catalyzes the breakdown of superoxide ions to oxygen and hydrogen peroxide, which in turn is degraded by glutathione peroxidase or catalase to form water. Several lines of evidence argue that the mutant SOD1 protein is neurotoxic through an acquired, adverse function that entails both oxidative pathology and protein aggregation, with secondary disturbances of glutamate metabolism, mitochondrial function, axonal transport and calcium homeostasis [3]. That mutant SOD1 is toxic is strongly supported by the observation that transgenic expression of high levels of mutant SOD1 protein in mice produces a motor neuron disease phenotype, with age of onset and disease duration dependent on copy number [4].

To date, few therapeutic interventions have altered the motor neuron phenotype in the transgenic ALS mice. Although more than 100 small molecules have been tested to date, few have had even a marginal benefit (e.g. riluzole [5], celecoxib [6], arimoclomol [7]). By contrast, some forms of protein therapy have been beneficial. Thus, improvement in survival was produced by administering insulin-like growth factor 1 either transgenically [8] or through AAV2-delivery via IM injection and subsequent retrograde axonal transport to motor nerves [9]. Two other proteins that have shown therapeutic promise as neuroprotective agents are erythropoietin [10] and vascular endothelial factor (VEGF) [11, 12]. The latter is of interest because genetic analysis has implicated hypomorphic variants in the VEGF gene as a risk factor for ALS [13]. Moreover, mice that lack hypoxia-responsive promoter elements develop a slowly progressive motor neuron disease [14]. Subsequently, it was documented that lentiviral delivery of VEGF to the spinal cord of ALS mice delays death [15]. Two independent investigators have reported that infusion of VEGF into the cerebrospinal fluid in ALS mice [16] and rats [17] also slow the disease course.

Gene therapy is an emerging treatment modality for disorders affecting the central nervous system (CNS). CNS gene therapy has been facilitated by the development of viral vectors capable of effectively infecting post-mitotic neurons. The central nervous system is made up of the spinal cord and the brain. The spinal cord conducts sensory information from the peripheral nervous system to the brain and conducts motor information from the brain to various effectors. For a review of viral vectors for gene delivery to the central nervous system, see Davidson et al. (2003) Nature Rev. 4:353-364.

Adeno-associated virus (AAV) vectors are considered useful for CNS gene therapy because they have a favorable toxicity and immunogenicity profile, are able to transduce neuronal cells, and are able to mediate long-term expression in the CNS (Kaplitt et al. (1994) Nat. Genet. 8:148-154; Bartlett et al. (1998) Hum. Gene Ther. 9:1181-1186; and Passini et al. (2002) J. Neurosci. 22:6437-6446).

One useful property of AAV vectors lies in the ability of some AAV vectors to undergo retrograde and/or anterograde transport in neuronal cells. Neurons in one brain region are interconnected by axons to distal brain regions thereby providing a transport system for vector delivery. For example, an AAV vector may be administered at or near the axon terminals of neurons. The neurons internalize the AAV vector and transport it in a retrograde manner along the axon to the cell body. Similar properties of adenovirus, HSV, and pseudo-rabies virus have been shown to deliver genes to distal structures within the brain (Soudas et al. (2001) FASEB J. 15:2283-2285; Breakefield et al. (1991) New Biol. 3:203-218; and deFalco et al. (2001) Science, 291:2608-2613).

Several groups have reported that the transduction of the brain by AAV serotype 2 (AAV2) is limited to the intracranial injection site (Kaplitt et al. (1994) Nat. Genet. 8:148-154; Passini et al. (2002) J. Neurosci. 22:6437-6446; and Chamberlin et al. (1998) Brain Res. 793:169-175). Recent reports suggest that retrograde axonal transport of neurotrophic viral vectors, including AAV and lentiviral vectors, can also occur in select circuits of the normal rat brain (Kaspar et al. (2002) Mol. Ther. 5:50-56; Kasper et al. (2003) Science 301:839-842 and Azzouz et al. (2004) Nature 429:413-417. Roaul et al. (2005) Nat. Med. 11(4):423-428 and Ralph et al. (2005) Nat. Med. 11(4):429-433 report that intramuscular injection of lentivirus expressing silencing human Cu/Zn superoxide dismutase (SOD1) interfering RNA retarded disease onset of amyotrophic lateral sclerosis (ALS) in a therapeutically relevant rodent model of ALS.

Cells transduced by AAV vectors may express a therapeutic transgene product, such as an enzyme or a neurotrophic factor, to mediate beneficial effects intracellularly. These cells may also secrete the therapeutic transgene product, which may be subsequently taken up by distal cells where it may mediate its beneficial effects. This process has been described as cross-correction (Neufeld et al. (1970) Science 169:141-146).

There is a need in the art for compositions and methods to treat dysfunction of the spinal cord that result in loss of motor function in human patients.

SUMMARY OF THE INVENTION

In one aspect, the invention provides a method of treating a mammal with a motor neuron disorder by direct spinal cord injection of a neurotrophic vector encoding for a therapeutic molecule. In one embodiment, the neurothrophic vector is a recombinant expression vector encoding HIF1-alpha where the vector is a recombinant adeno-associated virus (AAV). It is delivered by direct injection into the parenchyma of the spinal cord of a mammal with a motor neuron disorder. The life expectancy of the mammal is thereby extended.

In another aspect the invention provides a method of treating a human patient with a motor neuron disorder by direct spinal cord injection of a neurotrophic vector encoding for a therapeutic molecule. In one embodiment, a recombinant AAV vector encoding HIF1-alpha fused to NFκB is delivered to a plurality of sites in spinal cord of a human patient with a motor neuron disorder. Life expectancy of the human patient is thereby extended.

According to another embodiment of the invention a recombinant AAV vector encoding HIF1-alpha is provided for treating patients with a motor neuron disorder. The motor neuron disorder may be ALS. The AAV vector may be a recombinant AAV2/7 or AAV2/8 vector encoding HIF1-alpha.

It is to be understood that both the foregoing general description and the following detailed description are exemplary and explanatory only and are not restrictive of the invention as claimed.

DETAILED DESCRIPTION OF THE INVENTION

Figure 1:
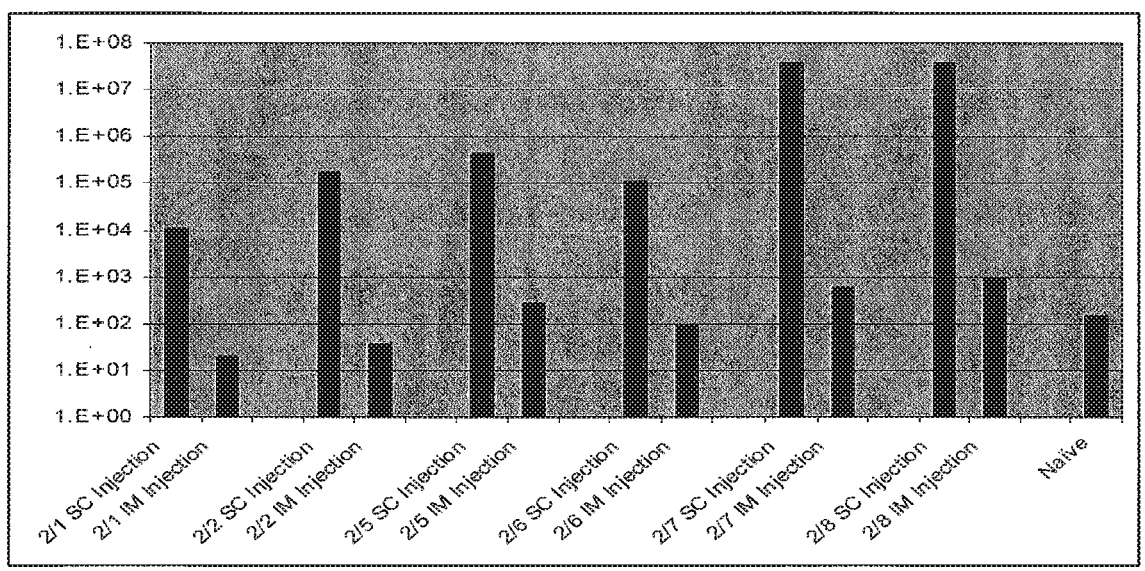
FIG. 1 shows spinal cord vector genome delivery via different delivery modes and vector pseudotypes.

In order that the present invention may be more readily understood, certain terms are first defined. Additional definitions are set forth throughout the detailed description.

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "transgene" refers to a polynucleotide that is introduced into a cell of and is capable of being transcribed into RNA and optionally, translated and/or expressed under appropriate conditions. In one aspect, it confers a desired property to a cell into which it was introduced, or otherwise leads to a desired therapeutic or diagnostic outcome.

The terms "genome particles (gp)," or "genome equivalents," as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278.

The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973.

The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay).

The terms "therapeutic," "therapeutically effective amount," and their cognates refer to that amount of an RNA, DNA or expression product of DNA and/or RNA that results in prevention or delay of onset or amelioration of symptoms of in a subject or an attainment of a desired biological outcome, such as correction of neuropathology, e.g., cellular pathology associated with a motor neuronal disease such as ALS. The term "therapeutic correction" refers to that degree of correction that results in prevention or delay of onset or amelioration of symptoms in a subject. The effective amount can be determined by known empirical methods.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term carrier further includes a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Additional carriers include polymeric excipients/additives such as polyvinylpyrrolidones, ficolls (a polymeric sugar), dextrates (e.g., cyclodextrins, such as 2-hydroxypropyl-.quadrature.-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives and any of the above noted carriers with the additional provision that they be acceptable for use in vivo. For examples of carriers, stabilizers and adjuvants, see Martin REMINGTON'S PHARM. SCI., 15th Ed. (Mack Publ. Co., Easton (1975) and Williams & Williams, (1995), and in the "PHYSICIAN'S DESK REFERENCE", $52^{nd}$ ed., Medical Economics, Montvale, N.J. (1998).

A "subject," "individual" or "patient" is used interchangeably herein, which refers to a vertebrate, preferably a mammal, more preferably a human. Mammals include, but are not limited to, murines, rats, simians, humans, farm animals, sport animals, and pets.

A "control" is an alternative subject or sample used in an experiment for comparison purpose. A control can be "positive" or "negative." For example, where the purpose of the experiment is to determine a correlation of an altered expression level of a gene with a particular type of pathology (see ALS, for example, infra), it is generally preferable to use a positive control (a subject or a sample from a subject, carrying such alteration and exhibiting symptoms characteristic of that disease), and a negative control (a subject or a sample from a subject lacking the altered expression and clinical symptom of that disease).

"Differentially expressed" as applied to a gene, refers to the differential production of the mRNA transcribed from the gene or the protein product encoded by the gene. A differentially expressed gene may be overexpressed or underexpressed as compared to the expression level of a normal or control cell. In one aspect, it refers to a differential that is at least 1.5 times, or at least 2.5 times, or alternatively at least 5 times, or alternatively at least 10 times higher or lower than the expression level detected in a control sample. The term "differentially expressed" also refers to nucleotide sequences in a cell or tissue which are expressed where silent in a control cell or not expressed where expressed in a control cell.

As used herein, the term "modulate" means to vary the amount or intensity of an effect or outcome, e.g., to enhance, augment, diminish or reduce.

As used herein the term "ameliorate" is synonymous with "alleviate" and means to reduce or lighten. For example one may ameliorate the symptoms of a disease or disorder by making them more bearable.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984. Wild-type AAV has high infectivity and specificity integrating into the host cell's genome. See, Hermonat and Muzyczka (1984) Proc. Natl. Acad. Sci. USA 81:6466-6470 and Lebkowski, et al. (1988) Mol. Cell. Biol. 8:3988-3996.

HIF-1 is a heterodimeric protein composed of two subunits: (i) a constitutively expressed beta (β) subunit (shared by other related transcription factors) and (ii) an alpha (α) subunit (see, e.g., WO 96/39426 describing the affinity purification and molecular cloning of HIF-1α) whose accumulation is regulated by a post-translational mechanism such that high levels of the alpha subunit can only be detected during hypoxic conditions. Both subunits are members of the basic helix-loop-helix (bHLH)-PAS family of transcription factors. These domains regulate DNA binding and dimerization. The transactivation domain is thought to reside in the C-terminus of the protein.

HIF-1 is involved in the regulation of a number of target genes (see e.g., Bracken et al., Cell. Mol. Life Sci. 60 (2003) 1376-1393 for a review of hypoxia inducible factors). Among the target genes for HIF-1 are VEGF and erythropoietin.

To stabilize the hypoxia inducible factor protein under normoxic conditions and to provide strong, constitutive transcriptional activation, a hybrid/chimeric fusion protein consisting of the DNA-binding and dimerization domains from HIF-1α at the amino terminus, and a functional transcriptional activator domain of a transcriptional activator protein at the carboxy terminus is utilized. To create this fusion protein, the endogenous transactivation domain of HIF-1α is replaced by a heterologous transactivation domain. In one embodiment, the transactivation domain is from the Herpes Simplex Virus (HSV) VP16 protein. This is termed herein a HIF1alpha-VP16 construct or fusion construct. In another embodiment, the transactivation domain is the NF-κB transactivation domain, which may be the human NF-κB transactivation domain. This is termed herein a HIF1alpha-NFκB construct or fusion construct. Any mammalian HIF1-alpha coding sequence can be used. The heterologous transactivation domain may also be one of the yeast transcription factors such as GAL4 and GCN4. HIF-1α constructs comprising human coding sequences may be advantageously used for delivery to humans.

Hypoxia (a state in which tissue or cellular $O_2$ demand exceeds supply) is a powerful modulator of gene expression. The physiologic response to hypoxia involves enhanced erythropoiesis (Jelkman, Physiol. Rev. 72:449-489 (1992)), neovascularization in ischemic tissues (White et al., Circ. Res. 71:1490-1500 (1992)) and a switch to glycolysis-based metabolism (Wolfe et al., Eur. J. Biochem. 135:405-412 (1983)). These adaptive responses either increase $O_2$ delivery or activate alternate metabolic pathways that do not require $O_2$. The gene products involved in these processes include, for example: (i) EPO, encoding erythropoietin, the primary regulator of erythropoiesis and thus a major determinant of blood $O_2$-carrying capacity (Jiang et al., J. Biol. Chem. 271(30):17771-78 (1996)); (ii) VEGF, encoding vascular endothelial growth factor, a primary regulator of angiogenesis and thus a major determinant of tissue perfusion (Levy et al., J. Biol. Chem. 270:13333 (1995); Liu et al., Circ. Res. 77:638 (1995); Forsythe et al., Mol. Cell. Biol. 16:4604 (1996)); (iii) ALDA, ENO1, LDHA, PFKL, and PGK1, encoding the glycolytic enzymes aldolase A, enolase 1, lactate dehydrogenase A, phosphofructokinase L, and phosphoglycerate kinase 1, respectively, which provide a metabolic pathway for ATP generation in the absence of $O_2$ (Firth et al., Proc. Natl. Acad. Sci., USA 91:6496 (1994); Firth et al., J. Biol. Chem. 270:21021 (1995); Semenza et al., J. Biol. Chem. 269:23757 (1994)); and (iv) HO1 and iNOS, encoding heme oxygenase 1 and inducible nitric oxide synthase, which are responsible for the synthesis of the vasoactive molecules carbon monoxide and nitric oxide, respectively (Lee et al., J. Biol. Chem. 272:5375; Melillo et al. J. Exp. Med. 182:1683 (1995)).

An important mediator of these responses is the interaction of a transcriptional complex comprising a DNA-binding hypoxia-inducible factor protein, with its cognate DNA recognition site, a hypoxia-responsive element (BRE) located within the promoter/enhancer elements of hypoxia-inducible genes. HREs consist of an hypoxia-inducible factor protein binding site (that contains the core sequence 5'-CGTG-3') as well as additional DNA sequences that are required for function, which in some elements includes a second binding site.

In one embodiment, the hypoxia-inducible factor protein is HIF-1α (e.g., human HIF-1α). In another embodiment, the DNA-binding domain of HIF-1α comprises amino acids 1-390 of human HIF-1α.

In one embodiment, the protein domain capable of transcriptional activation is not derived from a hypoxia-inducible factor protein. In another embodiment, the protein domain capable of transcriptional activation is derived from a protein selected from the group consisting of: HSV VP16; NFκB; a heat shock factor; p53; fos; v-jun; factor EF-C; HIV tat; HPV E2; Ad $E_1α$; Sp1; AP1; CTF/NF1; E2F1; HAP1; HAP2; MCM1; PHO2; GAL4; GCN4; and GAL11.

In one embodiment, the protein domain capable of transcriptional activation is synthetic. In another embodiment, the hypoxia-inducible factor protein is HIF-1α (e.g., human HIF-1α and the protein domain capable of transcriptional activation is a transcriptional activation domain from HSV VP16. In still another embodiment, the hypoxia-inducible factor protein is HIF-1α (e.g., human HIF-1α and the protein domain capable of transcriptional activation is a transcriptional activation domain from NFκB.

In one embodiment, the invention is a method of treating a neurodegenerative disorder in a subject, including ALS, comprising administering to the subject an effective amount of a nucleic acid molecule encoding a biologically active chimeric transactivator protein comprising the DNA-binding domain of a hypoxia-inducible factor protein and a protein domain capable of transcriptional activation.

In a preferred embodiment, the nucleic acid molecule encoding a biologically active chimeric transactivator protein comprises the DNA-binding domain of a hypoxia-inducible factor (HIF) protein and a protein domain capable of transcriptional activation.

HIF-1 is a heterodimeric protein composed of two subunits: (i) a constitutively expressed beta (β) subunit also known as aryl hydrocarbon nuclear translocator (ARNT) (which is shared by other related transcription factors (e.g., the dioxin/aryl hydrocarbon receptor (DR/AhR)); and (ii) an alpha (α) subunit (see, e.g., WO 96/39426, International Application No. PCT/US96/10251 describing the recent affinity purification and molecular cloning of HIF-1α) whose accumulation is regulated by a post-translational mechanism such that high levels of the alpha subunit can only be detected during hypoxic conditions. Both subunits are members of the basic helix-loop-helix (bHLH)-PAS family of transcription factors. These domains regulate DNA binding and dimerization. The transactivation domain resides in the C-terminus of the protein. The basic region consists of approximately 15 predominantly basic amino acids responsible for direct DNA binding. This region is adjacent to two amphipathic a helices, separated by a loop of variable length, which forms the primary dimerization interface between family members (Moore, A. W., et al., Proc. Natl. Acad. Sci. USA 97:10436-41 (2000)). The PAS domain, which is named after the first three proteins in which it was identified (Per, ARNT and Sim), encompasses 200-300 amino acids containing two loosely conserved, largely hydrophobic regions approximately 50 amino acids, designated PAS A and PAS B.

Whereas, HIF-1β (ARNT) is expressed constitutively at a high level, accumulation of HIF-1 in the cell is sensitive to $O_2$ concentration, such that high levels are detected only during hypoxia. This observation has led to a proposed mechanism for target gene activation whereby $O_2$ concentration is detected by a sensor protein and through a complex signaling mechanism leads to stabilization of the HIF-1α subunit. HIF-1α is then available to complex with HIF-1β and bind selectively to HRE sites in the promoter/enhancer of the target gene(s). Regions of the HIF-1α protein involved in conferring this response are thought to coincide with regions involved in transactivation.

Induction of HIF-1 activity in response to hypoxia is thought to occur via stabilization of the HIF-1α protein. Regions of HIF-1α involved in this response have been localized to the C-terminus of the protein and overlap the transactivation domain. For example, Jiang et al., J. Biol. Chem. 271(30):17771 78 (1996) showed that HIF-1α truncated at amino acid 390 lost transactivation activity but retained the ability to bind DNA and showed high levels of protein under both normoxic and hypoxic conditions. This result demonstrated that the transactivation domain and the region conferring instability with normoxia reside in the C-terminal half of the protein. Pugh et al., J. Biol. Chem. 272(17):11205 14 (1997) have further localized the regions involved to two areas, amino acids 549-582 and 775-826.

An approximately 200-amino acid domain, referred to as the "oxygen-dependent degradation domain" (ODD), mediates the degradation of HIF-1α (Huang, L., J. Gu, M. Schau, and H. Bunn. 1998. Proc. Natl. Acad. Sci. U.S.A. 95: 7987-92). Deletion of the ODD (HIF-1αODD) results in a constitutively active HIF-1α regardless of oxygen concentration (Huang, L., J. Gu, M. Schau, and H. Bunn. 1998. Proc. Natl. Acad. Sci. U.S.A. 95: 7987-92; U.S. Pat. No. 6,124,131).

In one embodiment, this invention provides nucleic acid molecules encoding biologically active chimeric transactivator proteins comprising a domain of the HIF-1α protein sufficient for DNA binding and dimerization with HIF-1β (ARNT) and a protein domain capable of transcriptional activation.

In mice, two HIF-1α transcripts (I.1 and I.2) are produced from different promoters, as opposed to alternate splicing (Wenger, R. H., et al., Eur. J. Biochem. 246:155-65 (1997). These transcripts are both efficiently translated independent of oxygen, but differ in that transcript I.1 encodes a protein lacking the first 12 amino-terminal amino acids and is expressed in a tissue-restricted manner, while 1.2 is ubiquitously expressed and encodes a full-length protein. In spite of these differences, no specificity in DNA binding or transactivation activity has been observed (Wenger, R. H., et al., Blood 91:3471-80 (1998); Gorlach, A., et al., Biochem. Biophys. Acta 1493:125-134 (2000)). Several splice variants of HIF-1α have also been observed in humans. For example, a HIF-1α splice variant that lacks exon 14 has been found to be present in skin and several cell lines (Gothie, E., et al., J. Biol. Chem. 275:6922-27 (2000)). This leads to a frame shift and encodes a shorter protein (736 amino acids) which, although still hypoxically inducible, lacks a carboxy-terminal TAD (C-TAD) and therefore is less active than wild-type HIF-1α (Gothie, E., et al., J. Biol. Chem. 275:6922-27 (2000)). A dominant-negative isoform lacking exons 11 and 12 has also been identified, which encodes a protein that is 516 amino acids long, stable in normoxia and displays no transactivation (Chun, Y. S., et al., Biochem. J. 362:71-79 (2002)). In addition, a zinc-induced splice variant lacking exon 12 also acts as a dominant negative, inhibiting HIF activity by binding to ARNT and preventing its nuclear accumulation (Chun, Y. S., et al., Biochem. Biophys. Res. Commun. 268:652-56 (2000)).

Representative sequences of human HIF-1α include, for example, Genbank Accession Nos. NM_001530 (transcript variant 1) and NM_181054 (transcript variant 2). Representative sequences of the human HIF-1β subunit include, for example, Genbank Accession Nos, NM_001668 (ARNT transcript variant 1), NM_178426 (ARNT transcript variant 2) and NM_178427 (ARNT transcript variant 3).

A closely related protein, HIF-2α (also termed endothelial PAS (EPAS), HIF-related factor (HRF) and member of PAS superfamily 2 (MOP2)) was identified shortly after HIF-1α was cloned (Tian, H., et al., Genes Dev. 11:72-82 (1997); Ema, M., et al., Proc. Natl. Acad. Sci. USA 94:4273-78 (1997); Flamme, I., et al., Mech. Dev. 63:51-60 (1997); Hogenesch, J. B., et al., Proc. Natl. Acad. Sci. USA 95:5474-79 (1998)). HIF-2α shares 48% amino acid identity with HIF-1α and lesser similarity with other members of bHLH/PAS domain family of transcription factors (representative HIF-2α human sequences are GenBank Accession Nos. NM_001430 and U81984; a representative HIF2α mouse sequence is GenBank Accession No. U81983). Like HIF-1α, HIF-2α was found to heterodimerize with ARNT and bind HREs (Tian, H., et al., Genes Dev. 11:72-82 (1997); Ema, M., et al., Proc. Natl. Acad. Sci. USA 94:4273-78 (1997)). Deletion analysis has demonstrated that both HIF-1α and HIF-2α share a common functional domain architecture. Specifically, in addition to the amino-terminal bHLH and PAS domains, HIF-1α and HIF-2α possess two transactivation domains (TADs) separated by a region termed the inhibitory domain (ID), which is responsible for normoxic repression of TAD activity. Overlapping the amino-terminal TAD (N-TAD) is an oxygen-dependent degradation domain (ODDD), which confers normoxic stability to the HIFα-proteins (Bracken, C. P., et al., CMLS. Cell. Mol. Life Sci. 60:1376-93 (2003)).

Human and murine HIF-2α share extensive primary amino acid sequence identity with HIF-1α (48%). Sequence conservation between the two proteins is highest in the bHLH (85%), PAS-A (68%), and PAS-B (73%) regions. A second region of sequence identity occurs at the extreme C termini of the HIF-1α and HIF-2α proteins. This conserved region in mHIF-1α has been shown to contain a hypoxia response domain (Li et al., J. Biol. Chem. 271(35):21262-67 (1996)). The high degree of sequence similarity between HIF-1α and HIF-2α suggests that they share common physiological function(s). Hypoxic conditions stimulate the ability of HIF-1α to transactivate target genes containing the HRE core sequence. The activity of HIF-2α is also enhanced in cells grown under hypoxic conditions.

RNA expression patterns have revealed that both HIF-1α and HIF-2α are largely ubiquitously expressed in human and mouse tissues in an oxygen-independent manner (Tian. H., et al., Genes Dev. 11:72-82 (1997); Ema, M., et al., Proc. Natl. Acad. Sci. USA 94:4273-78 (1997); Flamme, I., et al., Mech. Dev. 63:51-60 (1997); Wenger, R. H., et al., Kidney Int. 51:560-63 (1997); Wiesener, M. S., et al., Blood 92:2260-68 (1998)). Cell-type-specific expression pattern analysis has revealed, however, that in contrast to ubiquitous HIF-1α, HIF-2α mRNA is predominantly expressed in specific cell types, such as endothelial, epithelial, neuronal, fibroblasts and macrophage cells (Bracken, C. P., et al., CMLS. Cell. Mol. Life Sci. 60:1376-93 (2003)).

A third HIFα gene has also been discovered and been termed HIF-3α. Like HIF-1α and HIF-2α, HIF-3α is expressed by a variety of tissues, dimerizes with ARNT, binds to HRE DNA sequences and upregulates reporter expression in a hypoxia-inducible and ARNT-dependent manner (Gu, Y. Z., et al., Gene Expr. 7:205-13 (1998)). A splice variant of HIF-3α, termed inhibitory PAS (IPAS), has been identified. IPAS appears to lack endogenous transactivation activity but acts as a dominant-negative regulator of HIF, interacting with the amino-terminal region of HIF-1α and preventing DNA binding. Representative sequences of human HIF-3α are Genbank Accession Nos. NM_152794 (HIF-3α transcript variant 1), NM_152794 (HIF-3α transcript variant 2) and NM_022462 (HIF-3α transcript variant 3).

As described herein and is apparent to those of skill in the art, sequences of HIF-1α, HIF-2α and/or HIF-3α, including sequences of any known or discovered splice variants, can be used in the methods of the invention.

Much has been discovered about the regulation of HIF-α. Normoxic turnover of HIF-α is very rapid and results in essentially no detectable HIF-α protein under normoxic conditions (Wang, G. L., et al., Proc. Natl. Acad. Sci. USA 92:5510-14 (1995); Yu, A. Y., et al., Am. J. Physiol. 275: L818-L826 (1998); Huang, L. E., et al., Proc. Natl. Acad. Sci, USA 95:7987-92 (1998)). This normoxic stability is controlled by the central 200-amino acid ODDD that overlaps the N-TAD (Huang, L. E., et al., Proc. Natl. Acad. Sci. USA 95:7987-92 (1998)). The rapid accumulation of HIF-1α and HIF-2α that occurs in hypoxia is mediated by increased protein stability. In contrast, oxygen tension does not have a major effect on HIF-α transcription or translation (Wenger, R. H., et al., Kidney Int. 51:560-63 (1997); Huang, L. E., et al., Proc. Natl. Acad. Sci. USA 95:7987-92 (1998)); Huang, L. E., et al., J. Biol. Chem. 271:32253-59 (1996); Powell, J. D., et al., Biol. Reprod. 67:995-1002 (2002); Kallio, P. J., et al., Proc. Natl. Acad, Sci. USA 94:5667-72 (1997)). Similarly, oxygen does not significantly affect ARNT mRNA or protein levels, which are constitutively expressed (Huang, L. E., et al., Proc. Natl. Acad. Sci. USA 95:7987-92 (1998)); Huang, L. E., et al., J. Biol. Chem. 271:32253-59 (1996); Kallio, P. J., et al., Proc. Natl. Acad. Sci. USA 94:5667-72 (1997)).

Normoxic instability of HIF-α is mediated by polyubiquitylation and subsequent degradation by the proteasome. This has been demonstrated using proteasomal inhibitors or mutation of the E1 ubiquitin activating enzyme (Huang, L E., et al., Proc. Natl. Acad. Sci. USA 95:7987-92 (1998); Kallio, P. J., et al., J. Biol. Chem. 274:6519-25 (1999)). Thus, HIF-α is polyubiquitylated under normoxia with the level of ubiquitylation decreasing in hypoxia (Huang, L. E., et al., Proc. Natl. Acad. Sci. USA 95:7987-92 (1998); Kallio, P. J., et al., J. Biol. Chem. 274:6519-25 (1999); Sutter, C. H., et al., Proc. Natl. Acad. Sci. USA 97:4748-53 (2000)). In addition, HIF-1α has been shown to physically interact with the 20S proteasomal subunit PSMA7 (Cho, S., et al., FEBS Lett. 498:62-66 (2001)).

The von-Hippel-Lindau (VHL) tumor suppressor protein is a component of an E3 ubiquitin-protein ligase complex containing elongins B and C, Cu12 and Rbx1, and it is this capacity by which VHL mediates the proteasomal degradation of HIF-1α and HIF-2α (Lisztwan, J., et al., Genes Dev. 13:1822-33 (1999)). Support is provided by the finding that under normoxic conditions, HIF-1α is stable in VHL-deficient cells, however, normoxic protein stability is restored upon VHL transfection (Maxwell, P. H., et al., Nature 399:271-75 (1999); Cockman, M. E., et al., J. Biol. Chem. 275:25733-741 (2000)). VHL is able to exert this effect by binding to amino acids 517-571 or 380-417 of HIF-1α, in normoxia (amino acids 517-534 and 383-418 in HIF-2α) via its β domain, while the α domain binds elongins. Ubiquitin is then transferred to residues of HIF, marking the protein for proteasomal degradation (Cockman, M. E., et al., J. Biol. Chem. 275:25733-741 (2000); Ohh, M., et al., Nat. Cell Biol. 2:423-27 (2000)); Tanimoto, K., et al., EMBO J. 19:4298-4309 (2000); Masson, N., et al., EMBO J. 20:5197-5206 (2001); Srinivas, V., et al., Biochem. Biophys. Res. Commun. 260:557-61 (1999)).

It has been discovered that the binding of VHL to HIF in normoxia, and thus the major mechanism by which HIF protein instability is conferred, is mediated by the irreversible hydroxylation of two proline residues (P402 and P564 in HIF-1α, P405 and P530 in HIF-2α) (Jaakkola, P., et al., Science 292:468-72 (2001); Ivan, M., et al., Science 292: 464-68 (2001); Yu, F., et al., Proc. Natl. Acad. Sci. USA 98:9630-35 (2001)); Chan, D. A., et al., J. Biol. Chem. 277:40112-17 (2002)). These residues are hydroxylated only in normoxia, enabling the high-affinity binding of VHL to HIF (Min, J. H., et al., Science 296:1886-89 (2002)). The identification of eg19, a HIF prolyl-hydroxylase in *Caenorhabditis elegans*, enabled the cloning of three mammalian homologs designated prolyl-hydroxylase domain containing (PHDs) 1, 2 and 3, or HIF prolyl-hydroxylases (HPHs 3, 2 and 1, respectively (Bruick, R. K., et al., Science 294:1337-40 (2001); Epstein, A. C., et al., Cell 107:43-54 (2001); Ivan, M., et al., Proc. Natl. Acad. Sci. USA 99:13459-464 (2002); Lieb, M. E., et al., Biochem. Cell. Biol. 80:421-426 (2002); Huang, J., et al., J. Biol. Chem. 277:39792-800 (2002)). A widely expressed fourth PHD/HPH has also been identified (Oehme, F., et al., Biochem. Biophys. Res. Commun. 296(2):343-49 (2002)).

The PHD/HPHs are 2-oxogluterate-dependent enzymes that require oxygen ($O_2$) for hydroxylation. They contain iron bound to two histidine and one aspartic acid residue, which, when maintained in its ferrous state by ascorbate, binds dioxygen. One oxygen is transferred to the target proline residue of HIF; the second reacts with 2-oxogluterate to produce succinate and carbon dioxide. Thus, the absence of oxygen leads to no enzyme activity, nonmodification of HIF proline residues and no VHL/HIF binding, resulting in stabilized HIF-α protein.

Therefore, it is likely that PHD/HPHs function as a direct oxygen sensor in cells that directly modulate HIF in response to physiological oxygen concentration (Bracken, C. P., et al., CMLS. Cell. Mol. Life Sci. 60:1376-93 (2003)).

In one embodiment, the nucleic acid molecules encoding the chimeric transactivator proteins comprise a domain of a non-mammalian hypoxia-inducible factor protein. As will be recognized by the skilled artisan, the adaptive response to hypoxia is likely to have been highly conserved throughout evolution. Accordingly, hypoxia-inducible factor proteins would be expected to occur in a wide variety of species including non-mammalian vertebrates and non-vertebrates, such as insects. See, for example, Bacon et al., Biochem. Biophys, Res. Commun., 249:811-816 (1998), which reports the functional similarity between the Sima basic-helix-loop-helix PAS protein from Drosophila and the mammalian HIF-1α protein.

Nucleic acid and amino acid sequences for non-mammalian hypoxia-inducible factor proteins may be obtained by the skilled artisan by a variety of techniques, for example, by cross-hybridization or amplification using all or a portion of the sequences referred to herein. Once the sequence encoding a candidate hypoxia-inducible factor protein has been determined, the localization of portions of the protein sufficient to bind to HREs and dimerize with HIF-1β may be determined using, e.g., the same types of techniques used to determine the location of those domains within the human HIF-1α protein. Relevant domains of non-mammalian hypoxia-inducible factor proteins useful in the compositions and methods of this invention may also be produced synthetically or by site-directed manipulations of the DNA encoding known mammalian hypoxia-inducible factor proteins. It is also expected that the sequence motifs in common among various mammalian and non-mammalian hypoxia-inducible factor proteins will suggest consensus sequences that, while perhaps not occurring naturally in any species, would nevertheless produce domains useful in the methods and compositions of this invention. All that is required in order to substitute such non-mammalian hypoxia-inducible factor protein domains for the human HIF-1α protein domains exemplified herein is that they be able to bind to HREs and dimerize with HIF-1β (ARNT).

For example, although the HIF-1α subunit is unstable during normoxic conditions, overexpression of this subunit in cultured cells under normal oxygen levels is capable of inducing expression of genes normally induced by hypoxia. An alternative strategy would be to modify the HIF-1α subunit such that it no longer is destabilized by normoxic conditions and would therefore be more potent under a range of oxygen conditions.

Replacement of the C terminal (or transactivation) region of the hypoxia-inducible factor protein with a strong transactivation domain from a transcriptional activator protein such as, for example, Herpes Simplex Virus (HSV) VP16, NFκB or yeast transcription factors GAL4 and GCN4, is designed to stabilize the protein under normoxic conditions and provide strong, constitutive, transcriptional activation.

To stabilize the hypoxia-inducible factor protein under normoxic conditions and to provide strong, constitutive transcriptional activation, a hybrid/chimeric fusion protein consisting of the DNA-binding and dimerization domains from HIF-1α and the transactivation domain from Herpes Simplex Virus (HSV) VP16 protein was constructed. Administration of this hybrid/chimera to the cells of a subject via gene therapy induces the expression of genes normally up-regulated in response to hypoxia (i.e., VEGF and the like). A constitutively stable hybrid HIF-1α has been shown to be effective for treating ischemic patients (U.S. Pat. Nos. 6,432,927 and 7,053,062, both of which are incorporated by reference herein in their entirety).

Thus, as described and exemplified herein, administration of a nucleic acid molecule encoding a biologically active chimeric transactivator protein comprising the DNA-binding domain of a hypoxia-inducible factor protein (e.g., HIF-1α) and a protein domain capable of transcriptional activation (e.g., a transcriptional activation domain from HSV VP16, a transcriptional activation domain from NFκB) can treat neurodegenerative motor disorders in a patient in need thereof. In one embodiment, the DNA-binding domain is a DNA-binding domain of HIF-1α and the protein domain capable of transcriptional activation is a transcriptional activation domain of HSV VP16. A representative cDNA nucleic acid sequence of such a HIF-1α/VP16 construct, which contains the DNA-binding domain and HIF-1β dimerization domain of HIF-1α and the transcriptional activation domain of HSV VP16, is the following:

```
                                              (SEQ ID NO: 1)
ATGGAGGGCGCCGGCGGCGCGAACGACAAGAAAAAGATAAGT

TCTGAACGTCGAAAAGAAAAGTCTCGAGATGCAGCCAGATCTC

GGCGAAGTAAAGAATCTGAAGTTTTTTATGAGCTTGCTCATCAG

TTGCCACTTCCACATAATGTGAGTTCGCATCTTGATAAGGCCTC

TGTGATGAGGCTTACCATCAGCTATTTGCGTGTGAGGAAACTTC
```

-continued
```
TGGATGCTGGTGATTTGGATATTGAAGATGACATGAAAGCACA

GATGAATTGCTTTTATTTGAAAGCCTTGGATGGTTTTGTTATGGT

TCTCACAGATGATGGTGACATGATTTACATTTCTGATAATGTGA

ACAAATACATGGGATTAACTCAGTTTGAACTAACTGGACACAGT

GTGTTTGATTTTACTCATCCATGTGACCATGAGGAAATGAGAGA

AATGCTTACACACAGAAATGGCCTTGTGAAAAAGGGTAAAGAA

CAAAACACACAGCGAAGCTTTTTCTCAGAATGAAGTGTACCCT

AACTAGCCGAGGAAGAACTATGAACATAAAGTCTGCAACATGG

AAGGTATTGCACTGCACAGGCCACATTCACGTATATGATACCAA

CAGTAACCAACCTCAGTGTGGGTATAAGAAACCACCTATGACCT

GCTTGGTGCTGATTTGTGAACCCATTCCTCACCCATCAAATATT

GAAATTCCTTTAGATAGCAAGACTTTCCTCAGTCGACACAGCCT

GGATATGAAATTTTCTTATTGTGATGAAAGAATTACCGAATTGA

TGGGATATGAGCCAGAAGAACTTTTAGGCCGCTCAATTTATGAA

TATTATCATGCTTTGGACTCTGATCATCTGACCAAAACTCATCAT

GATATGTTTACTAAAGGACAAGTCACCACAGGACAGTACAGGA

TGCTTGCCAAAAGAGGTGGATATGTCTGGGTTGAAACTCAAGC

AACTGTCACATATAACACCAAGAATTCTCAACCACAGTGCATTG

TATGTGTGAATTACGTTGTGAGTGGTATTATTCAGCACGACTTG

ATTTTCTCCCTTCAACAAACAGAATGTGTCCTTAAACCGGTTGA

ATCTTCAGATATGAAAATGACTCAGCTATTCACCAAAGTTGAAT

CAGAAGATACAAGTAGCCTCTTTGACAAACTTAAGCCGGAATTC

CCGGGGATCTGGGCCCCCCCGACCGATGTCAGCCTGGGGGACG

AGCTCCACTTAGACGGCGAGGACGTGGCGATGGCGCATGCCGA

CGCGCTAGACGATTTCGATCTGGACATGTTGGGGGACGGGGATT

CCCCGGGGCCGGGATTTACCCCCCACGACTCCGCCCCCTACGGC

GCTCTGGATATGGCCGACTTCGAGTTTGAGCAGATGTTTACCGA

TGCCCTTGGAATTGACGAGTACGGTGGGTAG.
```

In this representative nucleic acid sequence, the sequence of the HIF-1α DNA-binding and HIF-1β dimerization domains is the following:

```
                                              (SEQ ID NO: 2)
ATGGAGGGCGCCGGCGGCGCGAACGACAAGAAAAAGATAAGT

TCTGAACGTCGAAAAGAAAAGTCTCGAGATGCAGCCAGATCTC

GGCGAAGTAAAGAATCTGAAGTTTTTTATGAGCTTGCTCATCAG

TTGCCACTTCCACATAATGTGAGTTCGCATCTTGATAAGGCCTC

TGTGATGAGGCTTACCATCAGCTATTTGCGTGTGAGGAAACTTC

TGGATGCTGGTGATTTGGATATTGAAGATGACATGAAAGCACA

GATGAATTGCTTTTATTTGAAAGCCTTGGATGGTTTTGTTATGGT

TCTCACAGATGATGGTGACATGATTTACATTTCTGATAATGTGA

ACAAATACATGGGATTAACTCAGTTTGAACTAACTGGACACAGT
```

-continued
```
GTGTTTGATTTTACTCATCCATGTGACCATGAGGAAATGAGAGA

AATGCTTACACACAGAAATGGCCTTGTGAAAAAGGGTAAAGAA

CAAAACACACAGCGAAGCTTTTTTCTCAGAATGAAGTGTACCCT

AACTAGCCGAGGAAGAACTATGAACATAAAGTCTGCAACATGG

AAGGTATTGCACTGCACAGGCCACATTCACGTATATGATACCAA

CAGTAACCAACCTCAGTGTGGGTATAAGAAACCACCTATGACCT

GCTTGGTGCTGATTTGTGAACCCATTCCTCACCCATCAAATATT

GAAATTCCTTTAGATAGCAAGACTTTCCTCAGTCGACACAGCCT

GGATATGAAATTTTCTTATTGTGATGAAAGAATTACCGAATTGA

TGGGATATGAGCCAGAAGAACTTTTAGGCCGCTCAATTTATGAA

TATTATCATGCTTTGGACTCTGATCATCTGACCAAAACTCATCAT

GATATGTTTACTAAAGGACAAGTCACCACAGGACAGTACAGGA

TGCTTGCCAAAAGAGGTGGATATGTCTGGGTTGAAACTCAAGC

AACTGTCACATATAACACCAAGAATTCTCAACCACAGTGCATTG

TATGTGTGAATTACGTTGTGAGTGGTATTATTCAGCACGACTTG

ATTTTCTCCCTTCAACAAACAGAATGTGTCCTTAAACCGGTTGA

ATCTTCAGATATGAAAATGACTCAGCTATTCACCAAAGTTGAAT

CAGAAGATACAAGTAGCCTCTTTGACAAACTTAAG.
```

In this representative sequence, the sequence of the transcriptional activation domain of HSV VP16 is the following:

```
                                        (SEQ ID NO: 3)
CCGGAATTCCCGGGGATCTGGGCCCCCCCGACCGATGTCAGCCT

GGGGGACGAGCTCCACTTAGACGGCGAGGACGTGGCGATGGCG

CATGCCGACGCGCTAGACGATTTCGATCTGGACATGTTGGGGGA

CGGGGATTCCCCGGGGCCGGGATTTACCCCCACGACTCCGCCC

CCTACGGCGCTCTGGATATGGCCGACTTCGAGTTTGAGCAGA

CCGGAATTCCCGGGGATCTGGGCCCCCCCGACCGATGTCAGCCT

GGGGGACGAGCTCCACTTAGACGGCGAGGACGTGGCGATGGCG

CATGCCGACGCGCTAGACGATTTCGATCTGGACATGTTGGGGGA

CGGGGATTCCCCGGGGCCGGGATTTACCCCCACGACTCCGCCC

CCTACGGCGCTCTGGATATGGCCGACTTCGAGTTTGAGCAGATG

TTTACCGATGCCCTTGGAATTGACGAGTACGGTGGGTAG.
```

The invention encompasses other nucleic acids that encode biologically active chimeric transactivator proteins, for example, a protein comprising the DNA-binding and dimerization domains of HIF-1α and the transactivation domain from an NFκB) protein (e.g., a human NFκB) protein).

Eukaryotic transcription factors are often composed of separate and independent DNA-binding and transcriptional activator domains (Mitchell and Tjian, Science 245:371-378 (1989)). The independence of the domains has allowed for the creation of functional fusion proteins consisting of the DNA-binding and activating domains of heterologous proteins. Chimeric eukaryotic regulatory proteins, consisting of the lexa DNA-binding protein and the activation domain of the yeast transcription factor, GAL4, were constructed by Brent and Ptashne (Nature 312:612-615 (1985)). The use of fusion proteins has identified several types of protein domains which act as transcriptional activators. These domains have little amino acid similarity but often are characterized as being either highly acidic (as in the case of GAL4 and GNC4), glutamine-rich (as in the case of Sp1), or proline-rich (as in the case of NF1, Ma and Ptashne, Cell 51:113-119 (1987); Courey and Tjian (1988); Mermod et al., Cell 58:741-753 (1989)).

One of the most efficient activator domains known is contained in the carboxyl-terminal 100 amino acids of the Herpes Simplex Virus (HSV) virion protein 16 (VP16) (Sadowski et al., Nature 335:563-564 (1988); Triezenberg et al., Genes & Dev. 2:718-729 (1988)). VP16, also known as Vmw65 or alpha-gene trans-inducing factor, is a structural protein of HSV which activates transcription of the immediate early promoters of the virus, including those for ICPO and ICP4 (Campbell et al., J. Mol. Biol. 180:1-19 (1984); Kristie and Roizman, Proc. Natl. Acad. Sci., USA 81:4065-4069 (1984); Pellet et al., Proc. Natl. Acad. Sci., USA 82:5870-5874 (1985)). Although VP16 specifically activates promoters containing the so called TAATGARAT element, the specificity is endowed by a cellular DNA-binding protein(s) that is complexed with the amino terminal domains(s) of VP16 (McKnight et al., Proc. Natl, Acad. Sci., USA 84:7061-7065 (1987); Preston et al., Cell 52:425-434 (1988)).

The present invention provides nucleic acids encoding hybrid/chimeric transactivating proteins comprising a functional portion of a DNA-binding protein and a functional portion of a transcriptional activator protein. Such hybrid/chimeric transactivating proteins offer a variety of advantages, including specific activation of expression of hypoxia-inducible genes containing hypoxia responsive elements (HREs), thereby achieving exceptionally high levels of gene expression. Nucleic acids encoding such hybrid/chimeric transactivating proteins are capable of functioning in vertebrate cells and may encode naturally-occurring transcriptional transactivating proteins or domains of proteins (e.g., naturally-occurring transcriptional transactivating proteins or domains from eukaryotic cells including vertebrate cells), viral transactivating proteins or domains or any synthetic amino acid sequence that is able to stimulate transcription from a vertebrate promoter. Examples of such transactivating proteins include, but are not limited to, the lymphoid specific transcription factor identified by Muller et al. (Nature 336:544-551 (1988)), the fos protein (Lucibello et al., Oncogene 3:43-52 (1988)); v-jun protein (Bos et al., Cell 52:705-712 (1988)); factor EF-C (Ostapchuk et al., Mol. Cell. Biol. 9:2787-2797 (1989)); HIV-1 tat protein (Arya et al., Science 229:69-73 (1985)), the papillomavirus E2 protein (Lambert et al., J. Virol. 63:3151-3154 (1989)) the adenovirus E1A protein (reviewed in Flint and Shenk, Ann. Rev. Genet. (1989), heat shock factors (HSF1 and HSF2) (Rabindran, et al., PNAS 88:6906-6910 (1991)); the p53 protein (Levine, Cell 88:323-331 (1997), Ko and Prives, Genes Dev. 10:1054-1072 (1996)); Sp1 (Kadonaga, et al. Cell 51:1079-1090 (1987)); AP1 (Lee, et al., Nature 325: 368-372 (1987)); CTF/NF1 (Mermod, et al., Cell 58: 741-753 (1989)), E2F1 (Neuman, et al., Gene 173: 163-169 (1996)); HAP1 (Pfeifer, et al., Cell 56: 291-301 (1989)); HAP2 (Pinkham, et al., Mol. Cell. Biol. 7:578-585 (1987)); MCM1 (Passmore, et al., J. Mol. Biol. 204:593-606 (1988); PHO2 (Sengstag, and Hinnen, NAR 15:233-246 (1987)); and GAL11 (Suzuki et al., Mol. Cell. Biol. 8:4991-4999 (1988)). In particular embodiments of the invention, the transactivating protein is Herpes simplex virus VP16 (Sadowski et al., Nature 335:563-564 (1988); Triezenberg et al., Genes and Dev. 2:718-729 (1988)), NF.kappa.B ((Schmitz and Baeuerle, EMBO J. 10:3805-3817 (1991); Schmitz, et al., J. Biol. Chem. 269:25613-25620 (1994); and Schmitz, et al., J. Biol. Chem. 270:15576-15584 (1995)), and yeast activators GAL4 and GCN4.

Of course, the skilled artisan will understand that transcriptional activation domains useful in the compositions and methods of this invention may also be synthetic, i.e., based on a sequence that is not contained within a known, naturally-occurring protein. See, for example, Pollock and Gilman, PNAS 94:13388-13389 (1997), which teaches that transcriptional activation is an inherently flexible process in which there is little, if any, requirement for specific structures or stereospecific protein contacts. It also reviews the variety of different molecules that can function as transcriptional activators, including short peptide motifs (as small as eight amino acids), simple amphipathic helices and even mutagenized domains of proteins unrelated to transcriptional activation.

According to the invention, nucleic acid sequences encoding a DNA-binding domain and a transactivating domain are combined so as to preserve the respective binding and transactivating properties of each of the domains. In various embodiments of the invention, the nucleic acid encoding the transactivating protein, or a portion thereof capable of activating transcription, may be inserted into nucleic acid at a locus which does not completely disrupt the function of the encoded DNA-binding domain. Regions of hypoxia-inducible factor proteins that are not required for DNA-binding and dimerization functions and regions of proteins that are not required for transcriptional transactivating function are known and/or may be identified by methods known in the art, including, e.g., analysis of mapped mutations as well as identification of regions lacking mapped mutations, which are presumably less sensitive to mutation than other, more functionally relevant portions of the molecule. The appropriate recombinant constructs may be produced using standard techniques in molecular biology, including those set forth in Maniatis (Molecular Cloning: A Laboratory Manual (Cold Spring Harbor, N.Y., Cold Spring Harbor Laboratory (1989)).

The recombinant DNA construct encoding the chimeric transactivator protein may be placed under the control of (i.e., operatively linked to) a suitable promoter and/or other expression control sequence. It may be desirable for the transactivator protein to be placed under the control of a constitutively active promoter sequence, although the transactivator protein may also be placed under the control of an inducible promoter, such as the metallothionine promoter (Brinster et al., Nature 296:39-42 (1982)) or a tissue-specific promoter. Promoter sequences that can be used according to the invention include, but are not limited to, the SV40 early promoter region (Benoist and Chambon, Nature 290:304-310 (1981)), the promoter contained in the long terminal repeat of Rous sarcoma virus (Yamamoto, et al., Cell 22:787-797 (1980)), the herpes thymidine kinase promoter (Wagner et al., Proc. Natl. Acad. Sci., U.S.A. 78:144-1445 (1981)), the human cytomegalovirus (CMV) immediate early promoter/enhancer (Boshart et al., Cell 41:521-530 (1985)).

In one embodiment of the invention, the chimeric transactivator protein is encoded by pcDNA3/HIF/VP16/Af12. In another embodiment, the chimeric transactivator protein is encoded by pcDNA3/HIF/VP16/RI, which is identical to pcDNA3/HIF/VP16/Af12 except that the VP16 segment is inserted after codon 530 of the HIF-1α coding region.

According to the invention, the nucleic acids encoding hybrid/chimeric transactivator proteins may be utilized to specifically regulate the expression of genes containing hypoxia responsive elements (HREs). These HREs correspond to a nucleic acid sequence recognized and bound by the DNA-binding protein used as the backbone of the chimeric transactivator protein.

In general, the nucleic acids encoding chimeric transactivator proteins may be used to selectively control the expression of genes of interest. For example, and not by way of limitation, chimeric transactivator proteins may be placed under control of a constitutive promoter and may be used to constitutively increase the expression of a gene of interest associated with hypoxia responsive elements (HREs), for example, when it is desirable to produce a particular gene product in quantity in a cell culture or in a transgenic animal. Alternatively, the transactivator protein may be placed under the control of a tissue-specific promoter so that the gene of interest is expressed in a particular tissue. In alternative embodiments of the invention, the chimeric transactivator function is inducible, so that the expression of a gene of interest, via hypoxia responsive elements (HREs), may be selectively increased or decreased. For reviews of conditional and inducible transgene expression, see Fishman, Circ. Res., 82:837-844 (1998) and Fishman, Trends Cardiovasc. Med., 5:211-217 (1995).

For additional information on HIF1-alpha constructs see, for example, U.S. Pat. No. 6,432,947.

Amyotrophic lateral sclerosis (ALS) is a progressive, neurodegenerative condition involving the loss of large motor neurons in the brain and spinal cord. It is characterized by progressive weakness, atrophy and spasticity, leading to paralysis and respiratory failure within five years of onset. Familial ALS accounts for 10% of all ALS cases; approximately 25% of these cases are due to mutations in the Cu/Zn superoxide dismutase gene (SOD1) [1]. To date 109 different mutations have been identified in the SOD1 gene; these span all five exons [2]. Besides very rare mutations in genes for heavy neurofilament chain (NFH), dynactin, vesicular binding protein 1 gene and the ALSIN gene, SOD1 is the only major ALS susceptibility locus identified. SOD1 is a mainly cytoplasmic enzyme that catalyzes the breakdown of superoxide ions to oxygen and hydrogen peroxide, which in turn is degraded by glutathione peroxidase or catalase to form water. Several lines of evidence argue that the mutant SOD1 protein is neurotoxic through an acquired, adverse function that entails both oxidative pathology and protein aggregation, with secondary disturbances of glutamate metabolism, mitochondrial function, axonal transport and calcium homeostasis [3]. That mutant SOD1 is toxic is strongly supported by the observation that transgenic expression of high levels of mutant SOD1 protein in mice produces a motor neuron disease phenotype, with age of onset and disease duration dependent on copy number [4].

To date, few therapeutic interventions have altered the motor neuron phenotype in the transgenic ALS mice. Although more than 100 small molecules have been tested to date, few have had even a marginal benefit (e.g. riluzole [5], celecoxib [6], arimoclomol [7]). By contrast, some forms of protein therapy have been beneficial. Thus, significant improvement in survival was produced by administering insulin-like growth factor 1 (IGF-1) either transgenically [8] or through AAV2-delivery via IM injection and subsequent retrograde axonal transport to motor nerves [9]. Two other proteins that have shown therapeutic promise as neuroprotective agents are erythropoietin [10] and vascular endothelial factor (VEGF) [11, 12]. The latter is of particular interest because genetic analysis has implicated hypomorphic variants in the VEGF gene as a risk factor for ALS [13]. Moreover, mice that lack hypoxia-responsive promoter elements develop a slowly progressive motor neuron disease [14]. Subsequently, it was documented that lentiviral delivery of VEGF to the spinal cord of ALS mice delays death [15]. Two independent investigators have reported that infusion of VEGF into the cerebrospinal fluid in ALS mice [16] and rats [17] also slow the disease course.

For this reason, one embodiment of the instant invention is a method that increases the levels of the VEGF family of neurotrophic proteins and/or EPO comprising injecting a neurotrophic vector encoding for HIF-1α into the spinal cord region of a subject with ALS or another motor neuron disorder. The method may increases more than one such neurotrophic protein. Without being limited as to theory, delivery of a transgene encoding for HIF-1α will increase the expression of various targets genes of HIF-1 thus providing a benefit to motor neurons in sites of HIF-1α expression.

Without being limited as to theory, direct spinal cord injection of a neurotrophic vector also provides an advantage for the delivery of therapeutic molecules, such as HIF-1α, that function more efficiently when expressed directly in spinal cord cells. For example, neurotrophic vectors encoding for molecules such as short interfering RNA (siRNA) may be delivered to spinal cord cells via direct injection of the spinal cord. siRNA delivered in this manner may directly intracellularly exert effects on transduced spinal cord cells.

In addition, certain genetic motor neuron disorders, such as SMA, may be treated by direct injection of the spinal cord with a neurotrophic vector encoding for a therapeutic gene. The instant method of direct spinal cord injection provides a means to deliver recombinant virus directly to cells in the spinal cord area.

Suitable neurotrophic viral vectors for the practice of this invention include, but are not limited to adeno-associated viral vectors (AAV), herpes simplex viral vectors (U.S. Pat. No. 5,672,344) and lentiviral vectors.

In the methods of the invention, AAV of any serotype or pseudotype can be used. The serotype of the viral vector used in certain embodiments of the invention is selected from the group consisting of from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can he used. Furthermore, pseudotyped AAV vectors may also be utilized in the methods described herein. Pseudotyped AAV vectors are those which contain the inverted terminal repeats (ITRs) of one AAV serotype and the capsid of a second AAV serotype; for example, an AAV vector that contains the AAV2 capsid and the AAV1 ITRs (i.e. AAV1/2) or an AAV vector that contains the AAV5 capsid and the AAV2 ITRs (i.e. AAV2/5).

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may be maintained episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In an illustrative embodiment, AAV is AAV7 or AAV8. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). Additionally, AAV-based gene therapy targeted to cells of the CNS has been described in U.S. Pat. Nos. 6,180,613 and 6,503,888. Additional exemplary AAV vectors are recombinant AAV1, AAV2, AAV5, AAV6, AAV7 and AAV8 serotype vectors encoding human protein. Additional exemplary pseudotyped vectors may be AAV vectors AAV2/1, AAV2/2, AAV2/6, AAV2/5, AAV2/7 and AAV2/8.

In certain methods of the invention, the vector comprises a transgene operably linked to a promoter. The transgene encodes a biologically active molecule, expression of which in the CNS results in at least partial correction of neuropathology. The HIF1-alpha gene is well-known in the art. See, e.g., NM_001530. and NP_001521. NFκB transactivation sequences can be substituted for the HIF1-alpha transactivation sequence. See, e.g., NM_003998.

The level of transgene expression in eukaryotic cells is largely determined by the transcriptional promoter within the transgene expression cassette. Promoters that show long-term activity and are tissue- and even cell-specific are used in some embodiments. Non limiting examples of promoters include, but are not limited to, the cytomegalovirus (CMV) promoter (Kaplitt et al. (1994) Nat. Genet. 8:148-154), CMV/human β-globin promoter (Mandel et al. (1998) J. Neurosci. 18:4271-4284), GFAP promoter (Xu et al. (2001) Gene Ther. 8:1323-1332), the 1.8-kb neuron-specific enolase (NSE) promoter (Klein et al. (1998) Exp. Neurol. 150:183-194), chicken beta actin (CBA) promoter (Miyazaki (1989) Gene 79:269-277), the β-glucuronidase (GUSB) promoter (Shipley et al. (1991) Genetics 10:1009-1018), and ubiquitin promoters such as those isolated from human ubiquitin A, human ubiquitin B, and human ubiquitin C as described in U.S. Pat. No. 6,667,174. To prolong expression, other regulatory elements may additionally be operably linked to the transgene, such as, e.g., the Woodchuck Hepatitis Virus Post-Regulatory Element (WPRE) (Donello et al. (1998) J. Virol. 72:5085-5092) or the bovine growth hormone (BGH) polyadenylation site.

For some CNS gene therapy applications, it may be necessary to control transcriptional activity. To this end, pharmacological regulation of gene expression with viral vectors can been obtained by including various regulatory elements and drug-responsive promoters as described, for example, in Haberma et al. (1998) Gene Ther. 5:1604-16011; and Ye et al. (1995) Science 283:88-91.

In certain embodiments, the concentration or titer of the vector in the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^{9}$ tu/ml); or (c) 5, 6, 7, 8, 9, 10, 15, 20, 25, or 50 ($\times 10^{10}$ iu/ml).

In one aspect, the transgene encodes a biologically active molecule, expression of which in the CNS results in at least partial correction of neuropathology. In some embodiments, the therapeutic transgene product is an HIF1-alpha protein that alleviates and/or prevents the symptoms of ALS. See Raoul et al. (2005) Nat. Med. 11(4):423-428 and Ralph et al. (2005) Nat. Med. 11(4):429-433.

Additional or alternative transgenes can be used to express a therapeutic amount of insulin growth factor-1 (IGF-1), calbindin D28, parvalbumin, HIF1-alpha, SIRT-2, VEGF, SMN-1, SMN-2, and CNTF (Ciliary neurotrophic factor).

The subject invention provides methods to modulate, correct or augment motor function in a subject afflicted with motor neuronal damage. For the purpose of illustration only, the subject may suffer from one or more of amytrophic lateral sclerosis (ALS), spinal bulbar muscular atrophy, spinal muscular atrophy (SMA), spinal cerebellar ataxia, primary lateral sclerosis (PLS), or traumatic spinal cord injury.

Without being limited as to theory, the pathology associated with motor neuron damage may include motor neuron degeneration, gliosis, neurofilament abnormalities, loss of myelinated fibers in corticospinal tracts and ventral roots. Two types of onset are recognized: bulbar onset, which affects brainstem motor neurons, (affects the facial muscles, speech, and swallowing); and limb onset, which affects spinal cord motor neurons, is reflected by spasticity, generalized weakness, muscular atrophy, paralysis, and respiratory failure. In ALS, subjects have both bulbar and limb onset. In PLS, subjects have bulbar onset.

The ability to organize and execute complex motor acts depends on signals from the motor areas in the cerebral cortex, i.e., the motor cortex. Cortical motor commands descend in two tracts. The corticobular fibers control the motor nuclei in the brain stem that move facial muscles and the corticospinal fibers control the spinal motor neurons that innervate the trunk and limb muscles. The cerebral cortex also indirectly influences spinal motor activity by acting on the descending brain stem pathways.

The primary motor cortex lies along the precentral gyms in Broadmann's area (4). The axons of the cortical neurons that project to the spinal cord run together in the corticospinal tract, a massive bundle of fibers containing about 1 million axons. About a third of these originate from the precentral gyms of the frontal lobe. Another third originate from area 6. The remainder originates in areas 3, 2, and 1 in the somatic sensory cortex and regulate transmission of afferent input through the dorsal horn.

The corticospinal fibers run together with corticobulbar fibers through the posterior limb of the internal capsule to reach the ventral portion of the midbrain. They separate in the pons into small bundles of fibers that course between the pontine nuclei. They regroup in the medulla to form the medullary pyramid. About three-quarters of the corticospinal fibers cross the midline in the pyramidal decussation at the junction of the medulla and spinal cord. The crossed fibers descend in the dorsal part of the lateral columns (dorsolateral column) of the spinal cord, forming the lateral corticospinal tract. The uncrossed fibers descend in the ventral columns as the ventral corticospinal tract.

The lateral and ventral divisions of the corticospinal tract terminate in about the same regions of spinal gray matter as the lateral and medial systems of the brain stem. The lateral corticospinal tract projects primarily to motor nuclei in the lateral part of the ventral horn and to interneurons in the intermediate zone. The ventral corticospinal tract projects bilaterally to the ventromedial cell column and to adjoining portions of the intermediate zone that contain the motor neuorons that innervate axial muscles.

In one aspect, the disclosed methods include administering to the CNS of an afflicted subject a neurotrophic viral vector carrying a transgene encoding a therapeutic product and allowing the transgene to be expressed within the CNS near the administration site at a level sufficient to exert a therapeutic effect as the expressed protein is transported via the CSF throughout the CNS. In addition, the vector may comprise a polynucleotide encoding a biologically active molecule effective to treat the CNS disorder. Such biologically active molecules may comprise peptides including but not limited to native, fused, or mutated versions of full-length proteins, native, fused, or mutated versions of protein fragments, synthetic polypeptides.

In an illustrative embodiment, the administration is accomplished by direct injection of a high titer vector solution into the spinal cord of a subject or patient.

In some embodiments, the methods comprise administration of a high titer neurotrophic vector carrying a therapeutic transgene so that the transgene product is expressed at a therapeutic level at a first site within the spinal cord. In some embodiments, the viral titer of the composition is at least: (a) 5, 6, 7, 8, 9, 10, 15, 20, 25, or 50 ($\times 10^{12}$ gp/ml); (b) 5, 6, 7, 8, 9, 10, 15, 20, 25, or 50 ($\times 10^{9}$ tu/ml); or (c) 5, 6, 7, 8, 9, 10, 15, 20, 25, or 50 ($\times 10^{10}$ iu/ml).

In experimental mice, the total volume of injected AAV solution is for example, between 1 to 20 µl. For other mammals, including the human, volumes and delivery rates are appropriately scaled. Treatment may consist of a single injection per target site, or may be repeated in one or more sites. Multiple injection sites can be used. For example, in some embodiments, in addition to the first administration site, a composition containing a viral vector carrying a transgene is administered to another site which can be contralateral or ipsilateral to the first administration site. Injections can be single or multiple, unilateral or bilateral.

High titer AAV preparations can be produced using techniques known in the art, e.g., as described in U.S. Pat. No. 5,658,776 and Viral Vectors for Gene Therapy: Methods and Protocols, ed. Machida, Humana Press, 2003.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The examples do not in any way limit the invention.

EXAMPLES

Example 1. rAAV Viral Vector Delivery of Transgene to the Spinal Cord

To date there have been relatively few studies that systematically monitor patterns of distribution of different serotypes of rAAV to the nervous system. One of the most informative suggested that rAAV2/1 and rAAV2/5 tended to exhibit higher transduction than rAAV2/2. In addition, retrograde transport of rAAV1 and rAAV5 has been observed [20]. We therefore conducted initial experiments to determine the relative uptake and delivery of a number of AAV serotypes, using two routes of delivery, to cells in the spinal cord, focusing on motor neurons. These initial experiments compared intraparenchymal spinal cord injection of AAV encoding for GFP (green fluorescent protein) to the intramuscular injection of AAV encoding for GFP. Six different pseudotyped AAV vectors were assessed including serotypes 2/1, 2/2, 2/5, 2/6, 2/7, and 2/8.

Intraspinal Cord Injections.

Mice were anaesthetized by isoflurane inhalation and immobilized using a stereotaxic device. Groups of mice were injected with an AAV CBA-GFP vector; one group with each one of the following serotypes: AAV2/1, AAV2/2, AAV2/5, AAV2/6, AAV2/7 and AAV2/8. Each mouse received a total of 2.5 e 10 DNAse resistant particles (DRPs). The dose was injected by intraparenchymal injection into the following areas of the spinal cord the C6 region (within the cervical region), the T8/T9 region and the T13 region (within the thoracic region), and the L3/L4 region (within the lumbar region). Four microliters of virus were injected per site at a rate of 1 microliter/minute.

Intramuscular Injections.

Groups of mice were injected with an AAV CBA-GFP vector; one group with each one of the following serotypes AAV2/1, AAV2/2, AAV2/5, AAV2/6, AAV2/7 and AAV2/8. Each mouse received four injections of AAV; two injections into the quadriceps muscle and two injections into the gasctrocnemius muscle. Each mouse received a total dose of 2.5 e 10 DNAse resistant particles (DRPs).

Whole brain, spinal cord and muscles were dissected. DNA was extracted via Qiagen Dneasy™ kit. BGH (bovine growth hormone) Taqman™ assay analysis was conducted on the brain, spinal cord, and muscles using primers and probes against the BGH sequence in the AAV CBA-GFP vector to determine the number of vector genome copies in each tissue. Copy number of BGH out of total DNA was determined. Immunohistochemistry was also performed on the dissected spinal cords to detect each of the following: 1) GFP to measure transgene expression, 2) Glial fibrillary acidic protein (GFAP) to label glial cells, and 3) SM132 and NeuN to label neuronal cells.

FIG. 1 demonstrates the number of AAV vector genomes that were delivered to the spinal cord by either spinal injections or by intramuscular injections. More vector genomes were found in the spinal cords of mice treated with spinal injections AAV 2/7 and 2/8.

Figure 2:
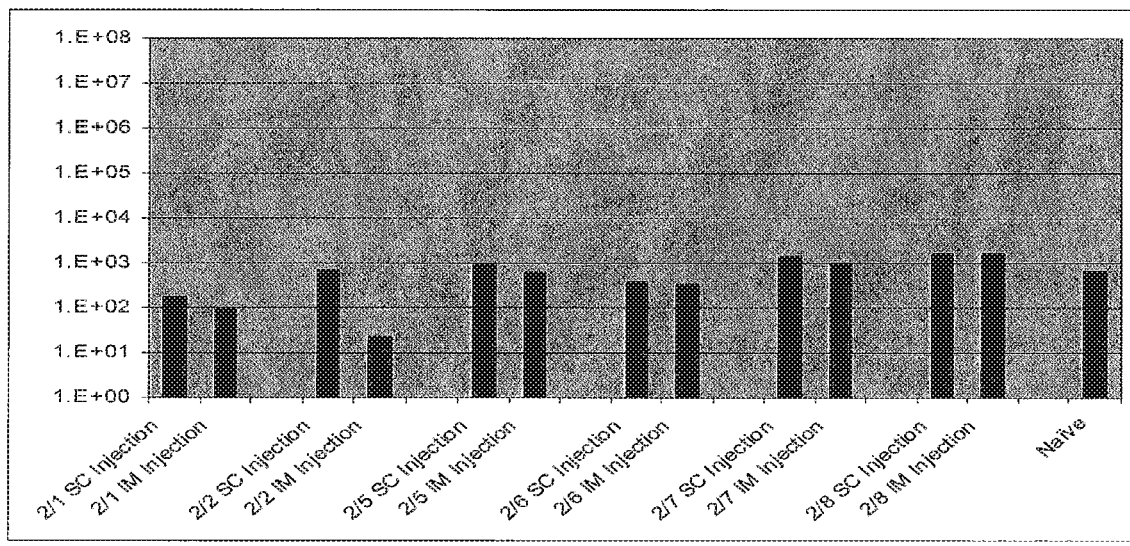
FIG. 2 shows brain vector genome delivery via different delivery modes and vector pseudotypes.

FIG. 2 shows the number of vector genomes that were delivered to the brain following either spinal cord or intramuscular injection of the AAV vectors. Very little AAV vector was present in the brain. Significant differences were not apparent among the different treatment groups. The data demonstrates that there was little dissemination of vector to the brain following direct spinal cord injection of any AAV serotype. This may be a safety advantage and suggests that vector remains in the area of the spinal cord following spinal cord injection.

Figure 3:
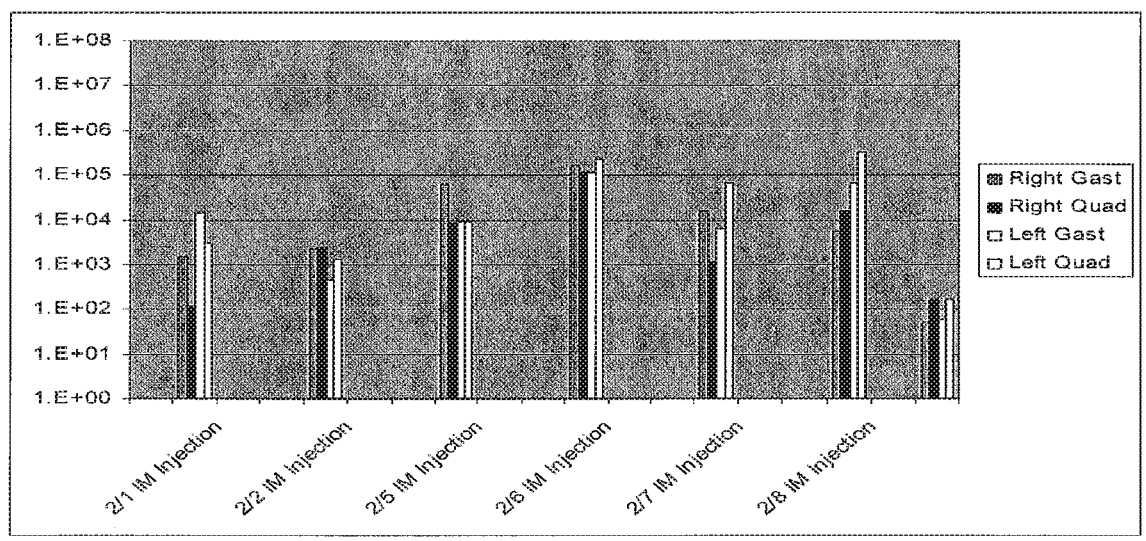
FIG. 3 shows the number of vector genomes that were delivered to the muscle following intramuscular injection of the AAV vectors.

FIG. 3 shows the number of vector genomes that were delivered to the muscle following intramuscular injection of the AAV vectors.

The data demonstrates that direct spinal cord injection of AAV vectors mediates greater gene transfer to the spinal cord as compared to intramuscular injection of the AAV vectors. This is demonstrated by the greater number of AAV vector genomes measured in the spinal cord in mice injected in spinal cord versus in the muscle with identical AAV vectors. In addition, the data demonstrates that the serotypes mediating the highest spinal cord gene transfer in this experiment were AAV2/7 and AAV2/8.

Immunohistochemistry results demonstrate that spinal cord injection of AAV vectors encoding for GFP resulted in significant GFP expression. GFP expression was co-localized on cells expressing neuronal markers, SM132 and NeuN. No co-localization of GFP was observed with GFAP, an astroglia marker. The immunohistochemical results were similar for all of the serotypes tested. Following intramuscular injection, no GFP or few GFP positive cells (mostly non-neuronal) were observed in the spinal cord after intramuscular injections.

Example 2. Evaluation of AAV-HIF-1alphaNFκB in the Mouse Brain

Injection of AAV-HIF1alphaNFκB in the Mouse Brain:

Mice were injected with AAV vectors encoding HIF1alphaNFκB in the thalamus area of the brain. Two serotypes were evaluated 1) AAV2/1-HIF1alphaNFκB and 2) AAV2-HIF1alphaNFκB. Each mouse received 9 e9 DNAse resistant particles (DRPs). Untreated mice served as controls. Four weeks post-injection, the mice were killed and their brains were collected. In situ hybridization was performed on brain sections to visualize HIF-1alpha mRNA. RT-PCR was also performed on cDNA extracted from the brains to evaluate VEGF gene expression. VEGF gene expression was normalized to GUSB gene expression.

HIF-1alpha mRNA was observed via in situ hybridization in brains of mice treated with both AAV2/1-HIF1alphaNFκB and AAV2-HIF1alphaNFκB; no message was observed in the control brains. More HIF-1alpha mRNA signal was observed in mice treated with AAV2/1-HIF1alphaNFκB. Gene expression analysis by RT-PCR demonstrated an increase in VEGF gene expression in mice treated with AAV2/1-HIF1alphaNFκB relative to control animals. No measurable increase in VEGF gene expression was observed in mice treated with AAV2-HIF1alphaNFκB.

In a second experiment, mice were injected with AAV2/1-HIF1alphaNFκB bilaterally into the cerebellum area of the mouse brain. Each mouse received 2 e10 DNAse resistant particles (DRPs). Untreated mice served as controls. Three weeks post-injection, the mice were killed and their brains were collected. In situ hybridization was performed on brain sections to visualize HIF-1alpha mRNA. RT-PCR was also performed on cDNA extracted from the brains to evaluate VEGF, EPO, and IGF-1 gene expression. Expression levels were normalized to GUSB gene expression.

Figure 4:
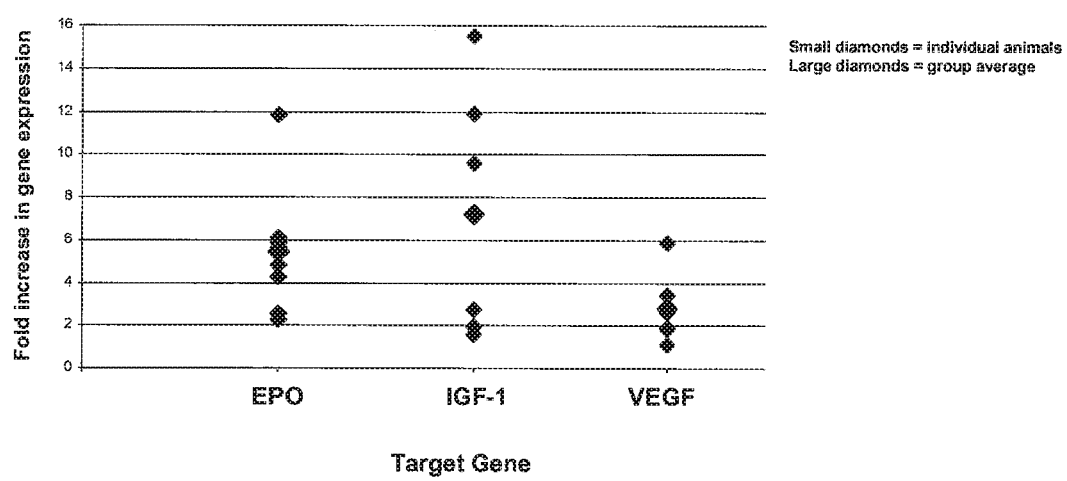
FIG. 4 shows gene expression of EPO, VEGF, and IGF-1 following transduction of a mouse brain with an AAV vector encoding for HIF-1 alpha NF-κB.
Figure 5:
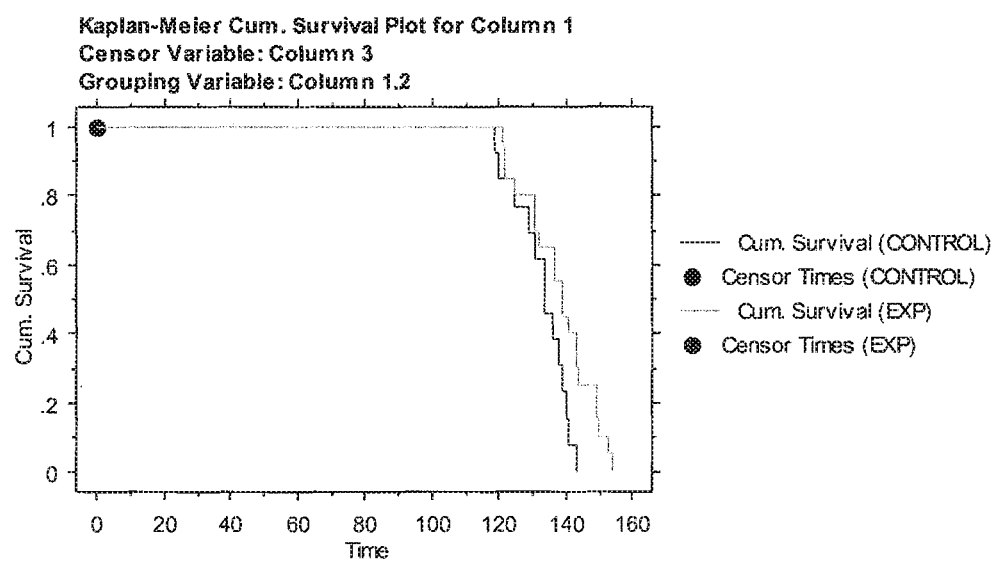
FIG. 5 shows a Kaplan-Meier survival curve that demonstrates a statistically significant (p=0.033) increase in survival of ALS mouse following intraspinal administration of AAV2/8 Hif1aNF-kB (133 days survival in control mice vs 139 day survival in Hif-1alpha NF-κB treated mice.)
Figure 6:
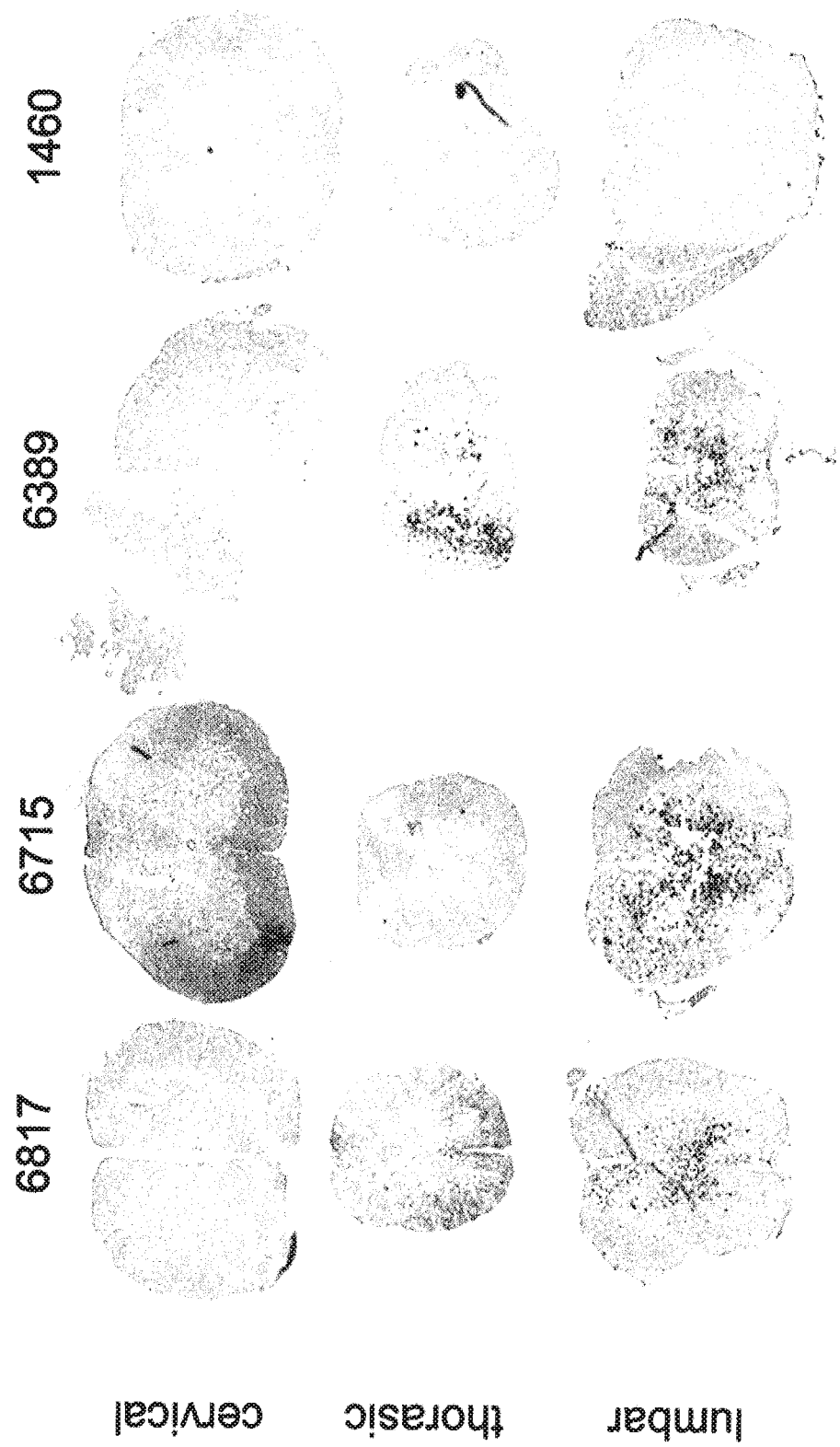
FIG. 6 shows in situ hybridization for Hif-1alpha NF-κB in the spinal cords of ALS mice treated with AAV2/8 Hif1aNFκB suggests that transduction was seen mainly in the lumbar region of the spinal cord. Animals 6817, 6715, and 6389 were treated with AAV2/8 Hif-1aNFκB; animal 1460 was a control animal.

HIF-1alpha mRNA was observed via in situ hybridization throughout the cerebellum. Expression was robust and was present throughout various neuronal cell layers. No HIF-1alpha mRNA was observed in the brainstem. HIF-1alpha mRNA was not observed in the brains of control mice. As shown in FIG. 4, VEGF, EPO, and IGF-1 mRNA levels were upregulated in the brain following transduction with an AAV vector encoding for HIF-1alpha. No upregulation in these genes was observed in control mice. This demonstrates that HIF-1alpha has the ability to modulate gene expression levels in target genes in the brain following transduction with an AAV vector.

Example 3. rAAV-Mediated Delivery of HIF-1alpha to the Spinal Cord of ALS Mice

Therapeutically Relevant Model of Amyotrophic Lateral Sclerosis (ALS). Amytrophic lateral sclerosis (ALS) is a fatal neurodegenerative disease that is characterized by a selective loss of motor neurons in the cortex, brain stem and spinal cord. Progression of the disease can lead to atrophy of limb, axial and respiratory muscles. Motor neuron cell death is accompanied by reactive gliosis, neurofilament abnormalities, and a significant loss of large myelinated fibers in the corticospinal tracts and ventral roots. Although the etiology of ALS is poorly understood, accumulating evidence indicates that sporadic (SALS) and familial (FALS) ALS share many similar pathological features; thus, providing a hope that the study of either form will lead to a common treatment. FALS accounts for approximately 10% of diagnosed cases, of which 20% are associated with dominantly inherited mutations in Cu/Zn superoxide dismutase (SOD1). Transgenic mice that express the mutant human SOD1 protein (e.g., SOD1$^{G93A}$ mice) recapitulate many pathological features of ALS and are an available animal model to study ALS. For SALS, a myriad of pathological mechanisms have been implicated as the underlying cause, including glutamate induced excitotoxicity, toxin exposure, proteasome dysfunction, mitochondrial damage, neurofilament disorganization and loss of neurotrophic support.

We will test the hypothesis that rAAV-mediated delivery of HIF1alpha to the spinal cord can promote motor neuron survival and ameliorate the disease progression of SOD1$^{G93A}$ ALS mice. Delivery with a recombinant AAV vector permits relatively long-term transgene expression (ALS mice may require transgene expression for many months. Moreover, depending on the serotype, AAV infects both neuronal and non-neuronal cells, a potential benefit if, as we suspect, non-neuronal cells participate in the death of the motor neurons [21].

Experimental Outline.

We used intraspinal injections to administer AAV2/8-HIF1alpha NFκB to determine of the effect of this strategy on motor neuron survival and disease onset and survival of ALS SOD1$^{G93A}$ mice.

rAAV Infection of Spinal Cord of ALS Mice.

For each viral treatment group, SOD1$^{G93A}$ or SOD1WT mice (5/group) and WT mice (5/group) either 60 days old or 90 days old were injected with 1 e 11 DRPs of AAV2/8-Hif1alpha-NFκB. As negative controls, SOD1 mice either 60 days old or 90 days old were injected with the same dose of empty vector. (As an additional positive control, SOD1 mice (5/group) either 60 days old or 90 days old could be injected with the same dose of AAV2/8-hIGF-1 (human IGF-1) vector. An additional negative control could also be wild-type mice.) Virus was injected into vertebrae C6, T8/T9, T13, L3/L4 of the spinal cord, 4 μl per site, delivered at 1 μl/min, with 2.5 e 10 DRP total dose. TaqMan assays will be used to detect viral genomes, message for HIF1alpha, and VEGF, in the spinal cord. In situ hybridization of spinal cords was performed to visualize HIF1-alpha expression in the spinal cords of both AAV2/8-Hif1alpha-NFκB treated and negative control mice.

Sample Size and Statistical Considerations.

Twenty TgSOD1$^{G93A}$ mice were treated with AAV2/8-HIF1alpha to be observed for onset and survival. An additional 30 mice of each type could be sacrificed for histological and biochemical analysis at 110d and terminally. Based on previous studies, we assume (i) mice with SOD1$^{G93A}$ transgene live 130±13 days; (ii) the statistical power of our study to detect the true-intergroup difference is 90%; (iii) alpha is two-tailed at 0.05; and (iv) we wish to detect a 10% or greater difference in mean survival of treated mice. With these assumptions, we require a minimum of 14 mice per test haplotype. We therefore elected to observe at least 20 animals in each group for onset, disease progression and survival, in case mice die for reasons unrelated to their motor neuron disease. In the final survival analysis, 20 mice treated with AAV2/8-HIP1alpha were evaluated and 18 control mice were evaluated. An additional 30 mice per group could be sacrificed for histological and biochemical analysis at pre-determined time intervals (5 per month×6 months). Time of disease onset and survival was compared using Kaplan-Meier plots and the log-rank statistical test. A Cox-proportional hazards model will be employed to control for the effects of gender.

Determination of the Effect of rAAV-HIF1alpha on the ALS Phenotype.

Disease onset is defined by the appearance of tremors in the outstretched legs when the mouse is held up by its tail. Death is defined as that point at which the mouse cannot right itself within 30 seconds.

Assessment of Effect of rAAV-HIF1alpha on Motor Neuron Survival.

We will use ventral root analysis to monitor motor neuron numbers on 5 TgSOD1$^{G93A}$ mice treated with rAAV-HIF1alpha at symptomatic (110 days) and end-stage time points.

Results.

A statistically significant (p=0.033) increase in survival of ALS mouse following intraspinal administration of AAV2/8 Hif1NFkB was observed (133 days survival control vs 139 day survival experimental animals). Different cohorts of animals responded differently to the treatment; 25% of the treated animals showed an increase in survival of 18-23 days while 25% of the animals showed an increase in survival of 8-13 days. In situ hybridization analysis for Hif1NFkB in the spinal cords of ALS mice treated with AAV2/8 Hif1NFkB suggests that transduction was seen mainly in the lumbar region of the spinal cord. In addition, the analysis suggests that only 25% of the intended dose of 1 e 11drps was given to the animals.

TABLE 1

Survival Summary Table for Column 1
Censor Variable: Column 3
Grouping Variable: Column 1.2

|  | # Obs. | # Events | # Censored | % Censored | # Missing | # Invalid |
| --- | --- | --- | --- | --- | --- | --- |
| CONTROL | 18 | 13 | 5 | 27.778 | 0 | 0 |
| EXP | 20 | 20 | 0 | 0.000 | 0 | 0 |
| Total | 38 | 33 | 5 | 13.158 | 0 | 0 |

TABLE 2

Kaplan-Meier Survival Statistics for Column 1
Censor Variable: Column 3
Grouping Variable: Column 1.2

|  | Estimate | Std. Error |
| --- | --- | --- |
| CONTROL: 25% | 129.000 | 4.992 |
| CONTROL: 50% | 134.000 | 2.996 |
| CONTROL: 75% | 139.000 | 1.519 |
| CONTROL: Mean | 133.000 | 2.169 |
| EXP: 25% | 131.000 | 4.782 |
| EXP: 50% | 139.000 | 2.966 |
| EXP: 75% | 144.000 | 3.873 |
| EXP: Mean | 138.100 | 2.334 |

Example 4. Hybrid/Chimera Construction

A hybrid transcription factor (pcDNA3/HIF.VP-16.Af12) composed of a DNA-binding and dimerization domain from HIF-1α and the transactivation domain from herpes simplex virus VP16 may be constructed to provide strong, constitutive activation of genes normally involved in the physiological adaptation to hypoxia as outlined below.

The full-length (aa 1-826) HIF-1 α gene was isolated by PCR (Advantage cDNA PCR Kit, Clontech, Palo Alto, Calif.) from a HeLa cell cDNA library (Clontech) using the primers set forth (SEQ ID NO:4: ggggtacctt ctcttctccg cgtgtggagg gagccagc; SEQ ID NO:5: gctctagagt gagccaccag tgtccaaaaa aaggatg) and inserted between the KpnI and XbaI sites of the expression vector, pcDNA3 (Invitrogen, Carlsbad, Calif.). In this plasmid, gene expression is controlled by the cytomegalovirus (CMV) immediate early enhancer/promoter. The HIF-1 α/VP-16 hybrid was constructed by truncating HIF-1 α at aa 390 (an Afl2 site) and then joining the transactivation domain of HSV VP-16 downstream. A VP16 fragment (aa 413-490) with Afl2 and XbaI ends was amplified by PCR using Vent polymerase (New England Biolabs, Beverly, Mass.) and the primers set forth (SEQ ID NO:6: cgtacgctta agccggaatt cccggggatc tgg; SEQ ID NO:7: cgctctagac tacccaccgt actcgtcaat tc) and this fragment was cloned into the appropriate sites of the pcDNA3/HIF-1α construct. A related construct (pcDNA3/HIF/VP-16/R1) was produced by truncating HIF-1α at aa 530 by partial digestion with EcoR1. The integrity of all sequences generated by PCR was verified by DNA sequencing using an Applied Biosystems 377 DNA Sequencer. All cloning manipulations were carried out following standard procedures (Sambrook, J. et al., Molecular Cloning, A Laboratory Manual 2d Ed. (Cold Spring Harbor, N.Y., 1989)). Restriction enzymes and DNA-modifying enzymes were obtained from ether New England Biolabs or Life Technologies, Inc. (Gaithersburg, Md.) and used according to the manufacturer's specifications. Plasmid DNAs were purified with kits obtained from Qiagen (Chatsworth, Calif.).

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may very depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

REFERENCES

1. Rosen, D. R., et al., *Mutations in Cu/Zn superoxide dismutase gene are associated with familial amyotrophic lateral sclerosis*. Nature, 1993. 362: p. 59-62.
2. Andersen, P. M., et al., *Sixteen novel mutations in the Cu/Zn superoxide dismutase gene in amyotrophic lateral sclerosis: a decade of discoveries, defects and disputes*. Amyotroph Lateral Scler Other Motor Neuron Disord, 2003. 4(2): p. 62-73.
3. Cleveland, D. W. and J. D. Rothstein, *From Charcot to Lou Gehrig: deciphering selective motor neuron death in ALS*. Nat Rev Neurosci, 2001. 2(11): p. 806-19.
4. Gurney, M. E., et al., *Motor neuron degeneration in mice that express a human Cu,Zn superoxide dismutase mutation*. Science, 1994. 264: p. 1772-1775.
5. Gurney, M. E., et al., *Benefit of vitamin E, riluzole, and gabapentin in a transgenic model of familial amyotrophic lateral sclerosis [see comments]*. Ann Neurol, 1996. 39(2): p. 147-57.
6. Drachman, D. B., et al., *Cyclooxygenase 2 inhibition protects motor neurons and prolongs survival in a transgenic mouse model of ALS*. Ann Neurol, 2002. 52(6): p. 771-8.
7. Kieran, D., et al., *Treatment with arimoclomol, a coinducer of heat shock proteins, delays disease progression in ALS mice*. Nat Med, 2004. 10(4): p. 402-5.
8. Dobrowolny, G., et al., *Muscle expression of a local Igf-1 isoform protects motor neurons in an ALS mouse model*. J Cell Biol, 2005. 168(2): p. 193-9.
9. Kaspar, B. K., et al., *Retrograde viral delivery of IGF-1 prolongs survival in a mouse ALS model*. Science, 2003. 301(5634): p. 839-42.
10. Iwasaki, Y., et al., *Protective effect of interleukin-3 and erythropoietin on motor neuron death after neonatal axotomy*. Neurol Res, 2002. 24(7): p. 643-6.
11. Brockington, A., et al., *Vascular endothelial growth factor and the nervous system*. Neuropathol Appl Neurobiol, 2004. 30(5): p. 427-46.
12. Storkebaum, E., D. Lambrechts, and P. Carmeliet, *VEGF: once regarded as a specific angiogenic factor, now implicated in neuroprotection*. Bioessays, 2004. 26(9): p. 943-54.
13. Lambrechts, D., et al., *VEGF is a modifier of amyotrophic lateral sclerosis in mice and humans and protects motoneurons against ischemic death*. Nat Genet, 2003. 34(4): p. 383-94.
14. Oosthuyse, B., et al., *Deletion of the hypoxia-response element in the vascular endothelial growth factor promoter causes motor neuron degeneration*. Nat Genet, 2001. 28(2): p. 131-8.
15. Azzouz, M., et al., *VEGF delivery with retrogradely transported lentivector prolongs survival in a mouse ALS model*. Nature, 2004. 429(6990): p. 413-7.
16. Zheng, C., et al., *Vascular endothelial growth factor prolongs survival in a transgenic mouse model of ALS*. Ann Neurol, 2004. 56(4): p. 564-7.
17. Storkebaum, E., et al., *Treatment of motoneuron degeneration by intracerebroventricular delivery of VEGF in a rat model of ALS*. Nat Neurosci, 2005. 8(1): p. 85-92.
18. Yamakawa, M., et al., *Hypoxia-inducible factor-1 mediates activation of cultured vascular endothelial cells by inducing multiple angiogenic factors*. Circ Res, 2003. 93(7): p. 664-73.
19. Vincent, K. A., et al., *Angiogenesis is induced in a rabbit model of hindlimb ischemia by naked DNA encoding an HIF-1alpha/VP16 hybrid transcription factor*. Circulation, 2000. 102(18): p. 2255-61.
20. Burger, C., et al., *Recombinant AAV viral vectors pseudotyped with viral capsids from serotypes 1, 2, and 5 display differential efficiency and cell tropism after delivery to different regions of the central nervous system*. Mol Ther, 2004. 10(2): p. 302-17.
21. Clement, A. M., et al., *Wild-type nonneuronal cells extend survival of SOD1 mutant motor neurons in ALS mice*. Science, 2003. 302(5642): p. 113-7.

We claim:

1. A recombinant gene delivery vector, comprising a recombinant AAV vector encoding a DNA binding domain of hypoxia-inducible factor 1-alpha (HIF 1-alpha) fused to a herpes simplex virus virion protein 16 (HSV VP 16) transcriptional activation domain, wherein the recombinant AAV vector comprises inverted terminal repeats of AAV-2 and an AAV-7 capsid or inverted terminal repeats of AAV-2 and an AAV-8 capsid, wherein the recombinant AAV vector is for treating patients with a motor neuron disorder, wherein the DNA binding domain of HIF 1-alpha fused to the HSV VP 16 transcriptional activation domain is encoded by the nucleotide sequence as shown in SEQ ID NO:1.

2. The vector of claim 1, wherein the recombinant AAV vector comprises inverted terminal repeats of AAV-2 and an AAV-7 capsid.

3. The vector of claim 1, wherein the recombinant AAV vector comprises inverted terminal repeats of AAV-2 and an AAV-8 capsid.

* * * * *